(12) United States Patent
Bachmann et al.

(10) Patent No.: US 10,493,444 B2
(45) Date of Patent: Dec. 3, 2019

(54) PIPETTING DEVICE FOR AN APPARATUS FOR PROCESSING A SAMPLE OR REAGENT, APPARATUS FOR PROCESSING A SAMPLE OR REAGENT AND METHOD FOR PIPETTING A SAMPLE OR REAGENT

(71) Applicant: Roche Molecular Systems, Inc., Pleasanton, CA (US)

(72) Inventors: Hans-Rudolf Bachmann, Buettikon (CH); Rolf Schneebeli, Mettmenstetten (CH); Geza Burghardt, Rotkreuz (CH); Kurt Barmettler, Lucerne (CH)

(73) Assignee: Roche Molecular Systems, Inc., Pleasanton, CA (US)

( * ) Notice: Subject to any disclaimer, the term of this patent is extended or adjusted under 35 U.S.C. 154(b) by 0 days.

(21) Appl. No.: 15/291,976

(22) Filed: Oct. 12, 2016

(65) Prior Publication Data

US 2017/0197208 A1    Jul. 13, 2017

(30) Foreign Application Priority Data

Oct. 13, 2015    (EP) .................................... 15189536

(51) Int. Cl.
*G01N 35/10*    (2006.01)
*B01L 3/02*    (2006.01)
*B01L 9/00*    (2006.01)

(52) U.S. Cl.
CPC .......... *B01L 3/0279* (2013.01); *B01L 3/0227* (2013.01); *G01N 35/1009* (2013.01);
(Continued)

(58) Field of Classification Search
CPC ............. G01N 35/1002; B01L 2200/16; B01L 2400/0487; B01L 3/02; B01L 2400/0478; B01L 9/543; Y10T 436/2575
See application file for complete search history.

(56) References Cited

U.S. PATENT DOCUMENTS 5,164,318 A * 11/1992 Sato ................. G01N 33/54306
422/504
5,434,083 A * 7/1995 Mitsumaki ......... G01N 35/0092
422/64
(Continued)

FOREIGN PATENT DOCUMENTS

EP    189900 A1    8/1986
EP    1058852 A1    12/2000
(Continued)

OTHER PUBLICATIONS

Extended European Search Report for EP15189536.4.
International Search Report dated Dec. 13, 2016.

*Primary Examiner* — Dennis White
*Assistant Examiner* — Bryan Kilpatrick
(74) *Attorney, Agent, or Firm* — Pamela Ancona; Eric Grant Lee

(57) ABSTRACT

A pipetting device (100) for an apparatus for processing a sample or reagent is disclosed. The pipetting device (100) comprises a coupling mechanism, wherein the coupling mechanism comprises at least a first coupling unit (104) adapted to be coupled to a first pipetting tip (108) and a second coupling unit (106) adapted to be coupled to a second pipetting tip (110), and a selection element (138) for selectively allowing a coupling of the first coupling unit (104) to or releasing the first coupling unit (104) from the first pipetting tip (108) and for selectively allowing a coupling of the second coupling unit to or releasing the second coupling unit (106) from the second pipetting tip (110). The selection element (138) is mechanically coupled to the first coupling unit (104) and the second coupling unit (106). Further, an apparatus (198) for processing a sample or reagent and a method for pipetting a sample or reagent are disclosed.

14 Claims, 20 Drawing Sheets

(52) U.S. Cl.
CPC ..... *G01N 35/1065* (2013.01); *G01N 35/1072* (2013.01); *G01N 35/1074* (2013.01); *G01N 35/1083* (2013.01); *B01L 3/02* (2013.01); *B01L 9/543* (2013.01); *B01L 2200/16* (2013.01); *B01L 2400/0487* (2013.01); *G01N 35/1002* (2013.01); *G01N 35/1004* (2013.01); *G01N 35/1016* (2013.01); *G01N 2035/103* (2013.01); *G01N 2035/1025* (2013.01); *G01N 2035/1086* (2013.01)

(56) References Cited

U.S. PATENT DOCUMENTS

| | | | |
|---|---|---|---|
| 5,525,302 | A | 6/1996 | Astle |
| 5,970,806 | A | 10/1999 | Telimma et al. |
| 6,994,828 | B2 | 2/2006 | Viot |
| 7,033,543 | B1 | 4/2006 | Panzer et al. |
| 7,434,484 | B2 | 10/2008 | Belgardt et al. |
| 7,947,234 | B2 | 5/2011 | O'Connell et al. |
| 2001/0036425 | A1 | 11/2001 | Gazeau et al. |
| 2001/0039843 | A1 | 11/2001 | Schoeppe |
| 2004/0228763 | A1 | 11/2004 | Ingenhoven et al. |
| 2007/0178016 | A1 | 8/2007 | Jost |
| 2007/0264725 | A1 | 11/2007 | Wiggli et al. |
| 2008/0240898 | A1 | 10/2008 | Manz et al. |
| 2014/0219887 | A1 | 8/2014 | Sheldon |

FOREIGN PATENT DOCUMENTS

| | | |
|---|---|---|
| EP | 1171240 B2 | 1/2002 |
| EP | 1241480 A2 | 9/2002 |
| EP | 2006021 A1 | 12/2008 |
| EP | 2410342 A2 | 1/2012 |
| EP | 2585834 A2 | 5/2013 |
| EP | 2691179 A1 | 2/2014 |
| WO | WO2014016282 A1 | 1/2014 |
| WO | WO2014027100 A1 | 2/2014 |

* cited by examiner

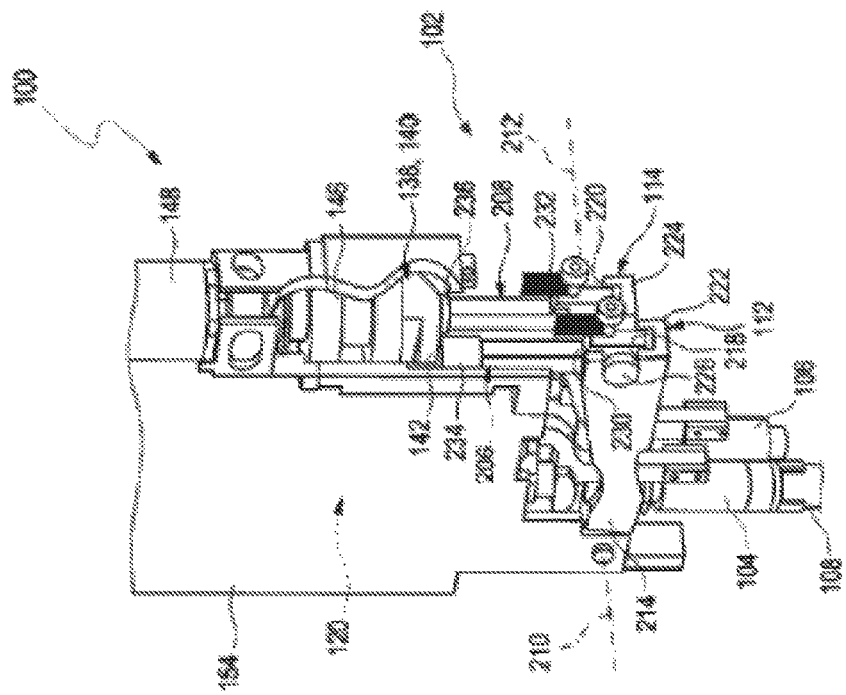
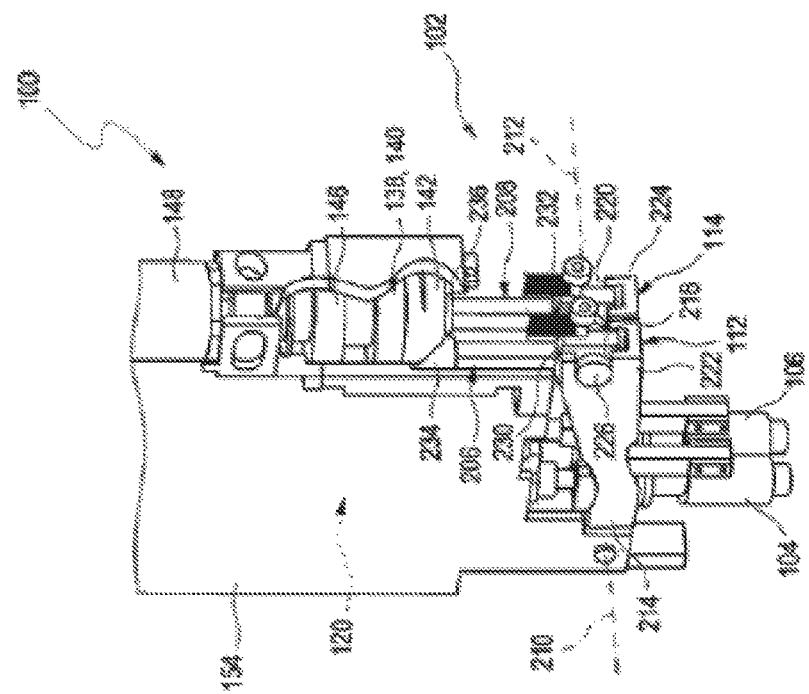

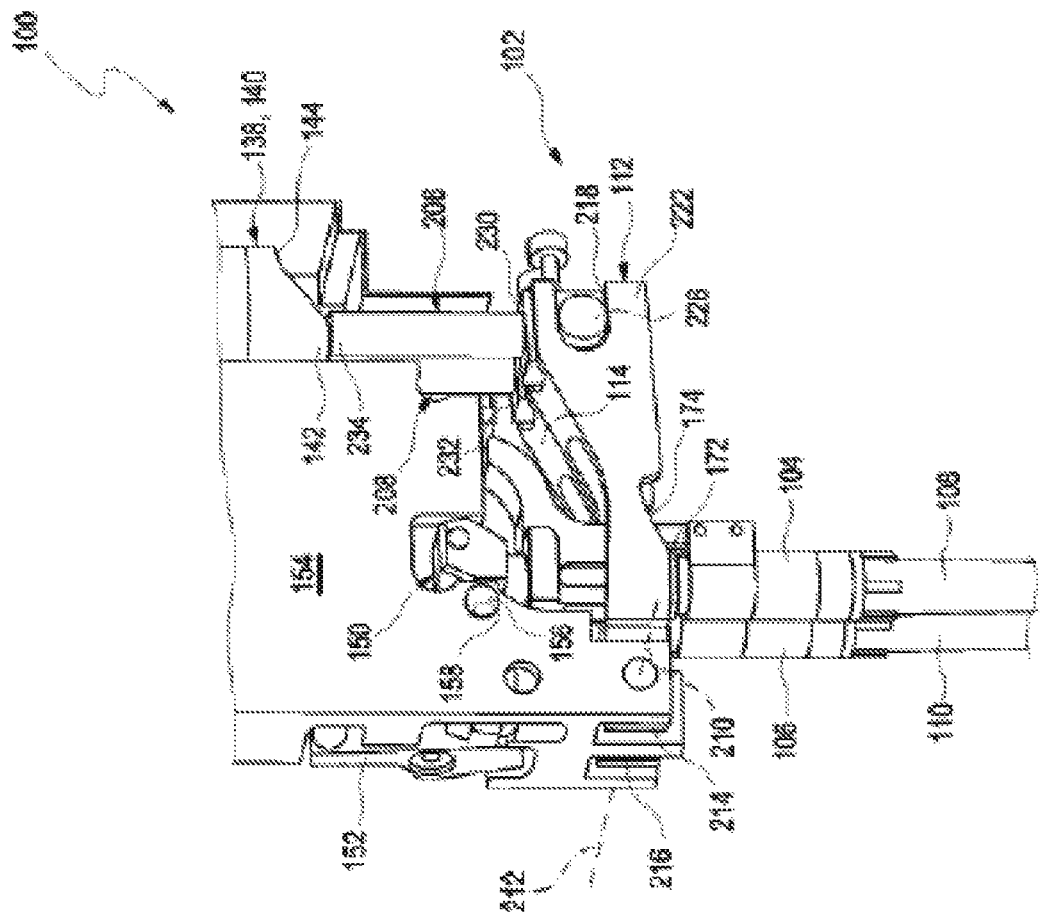

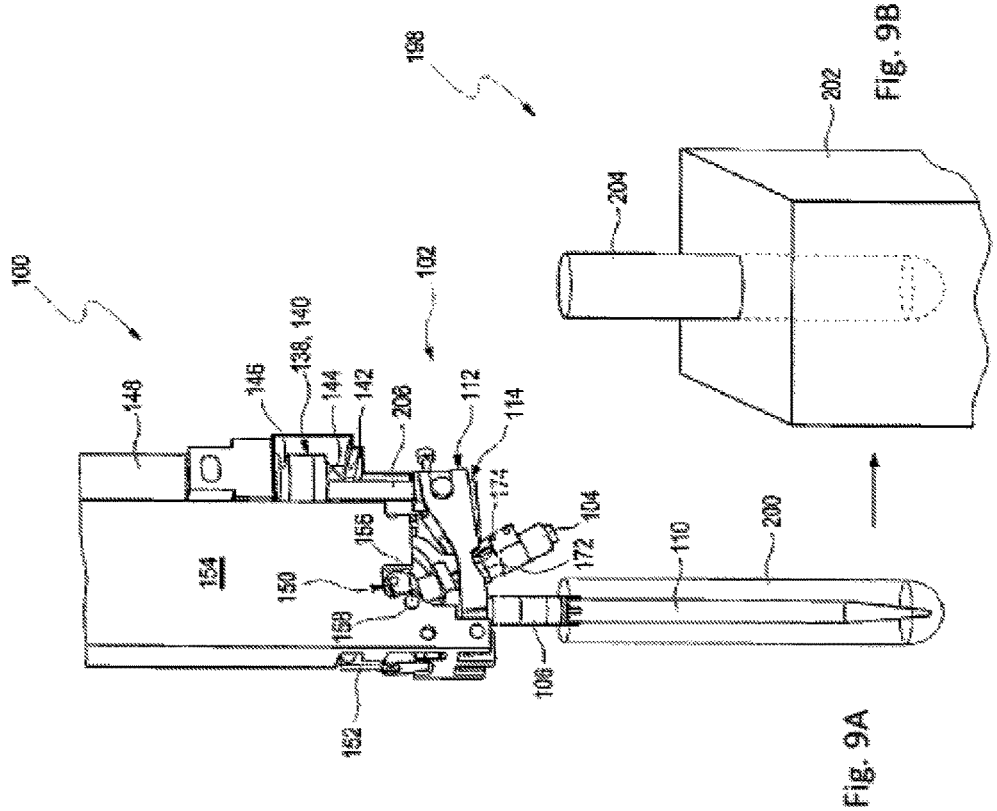

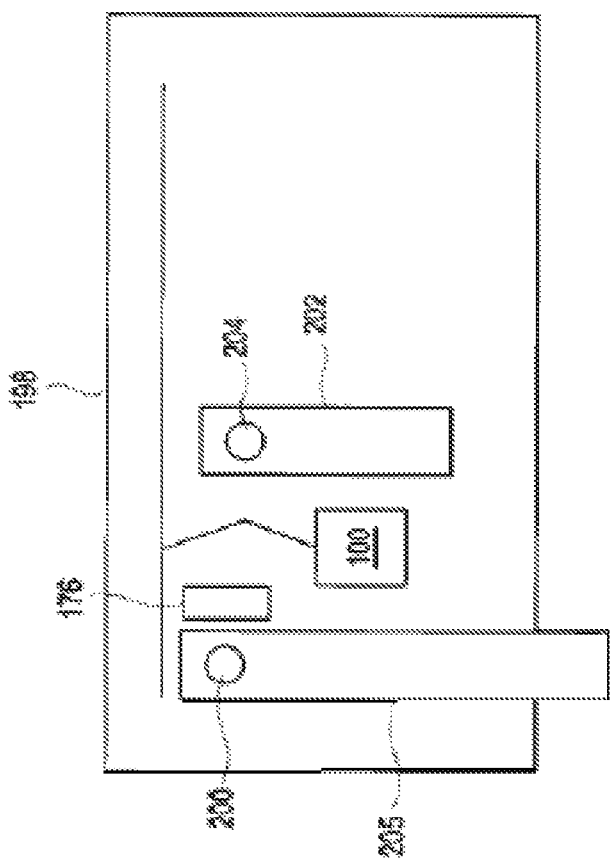

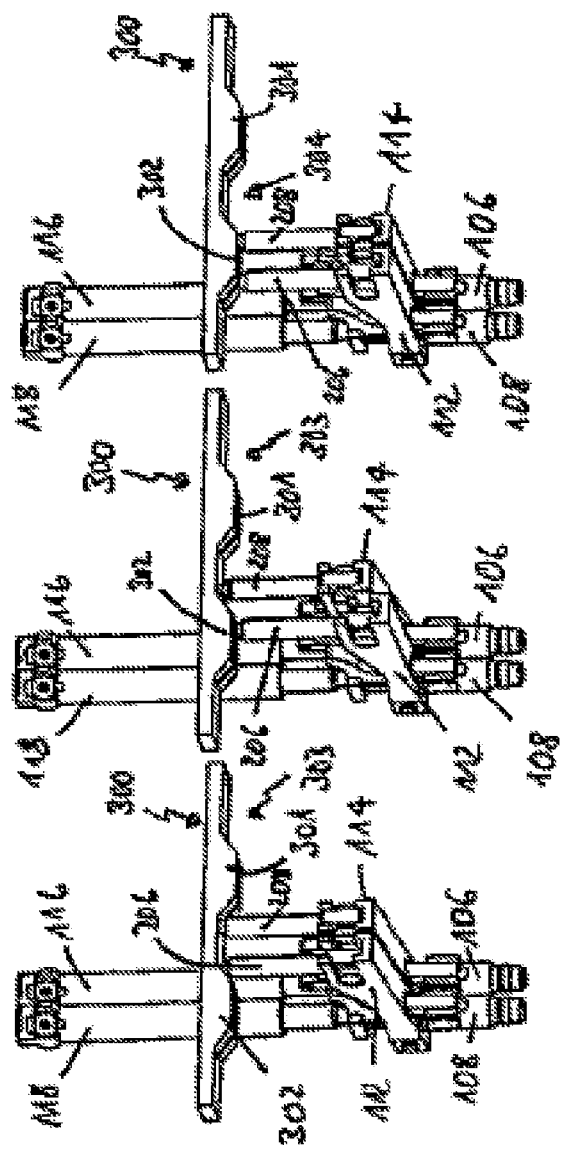

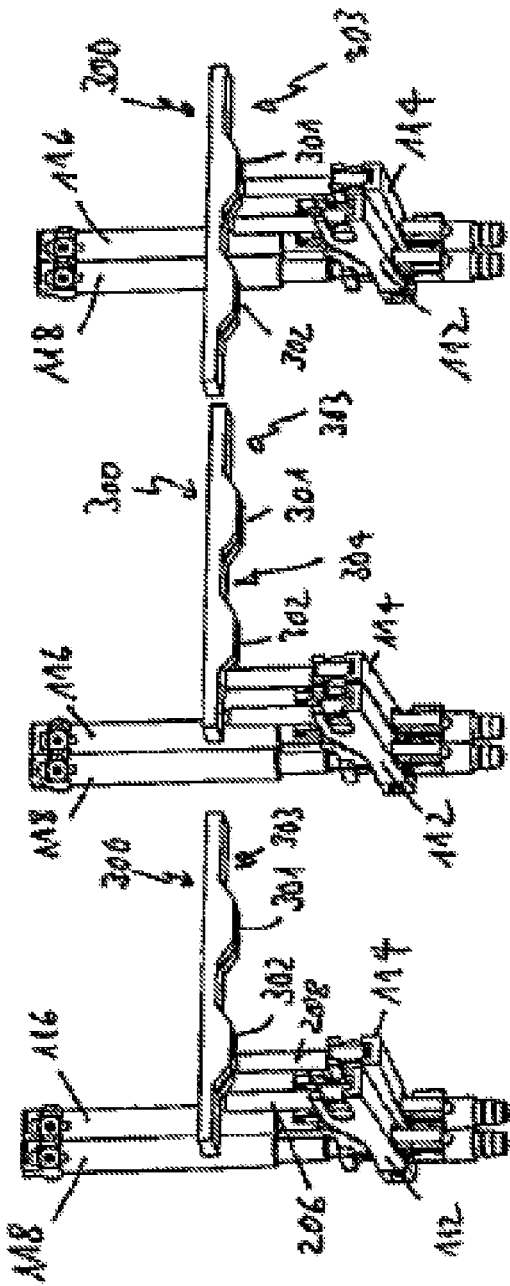

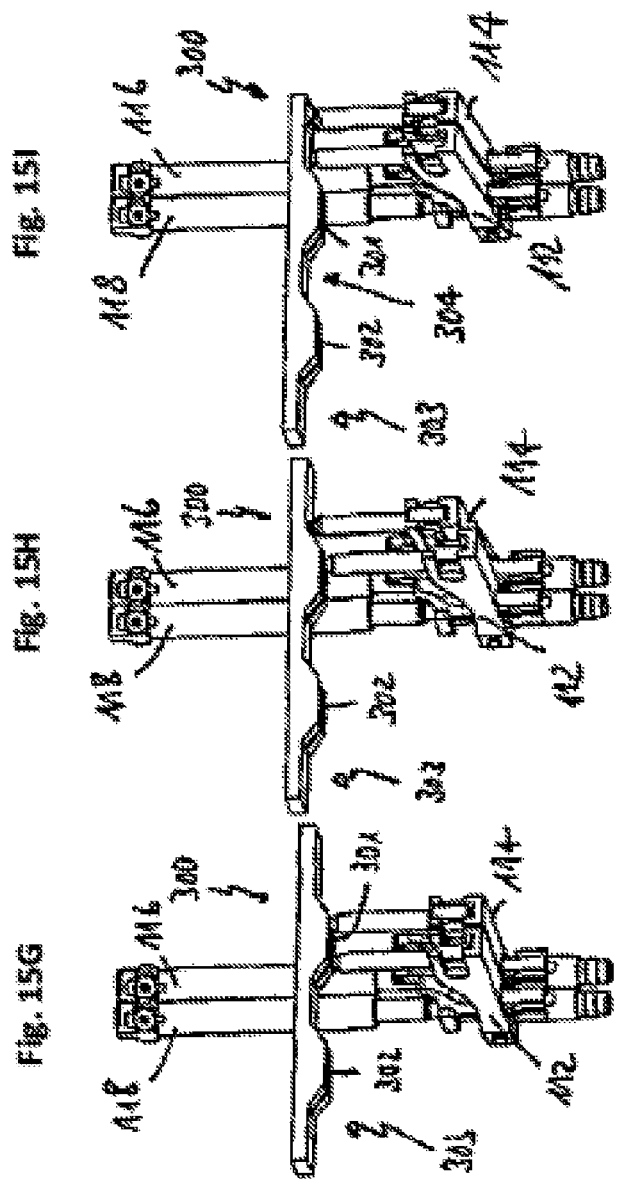

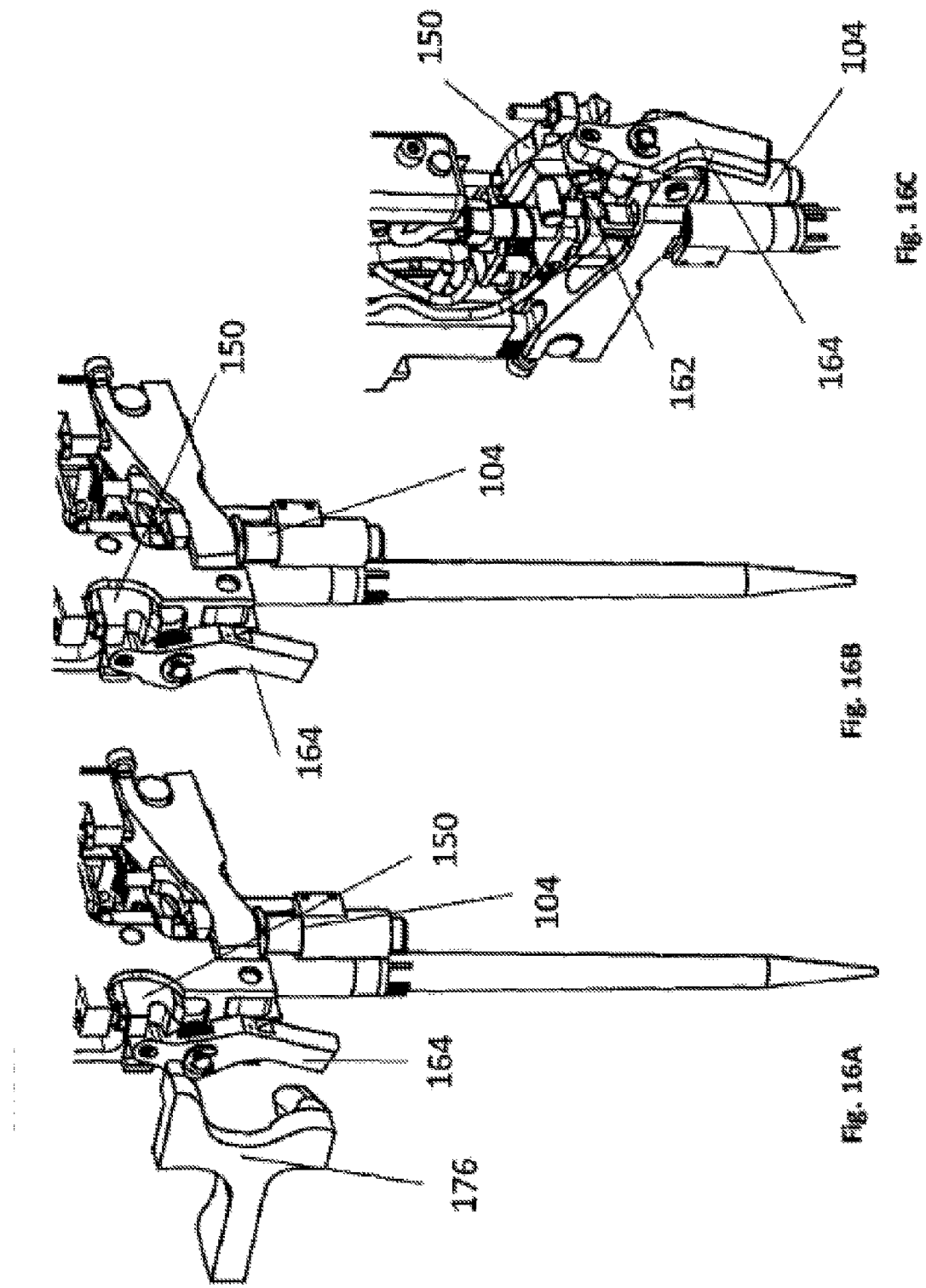

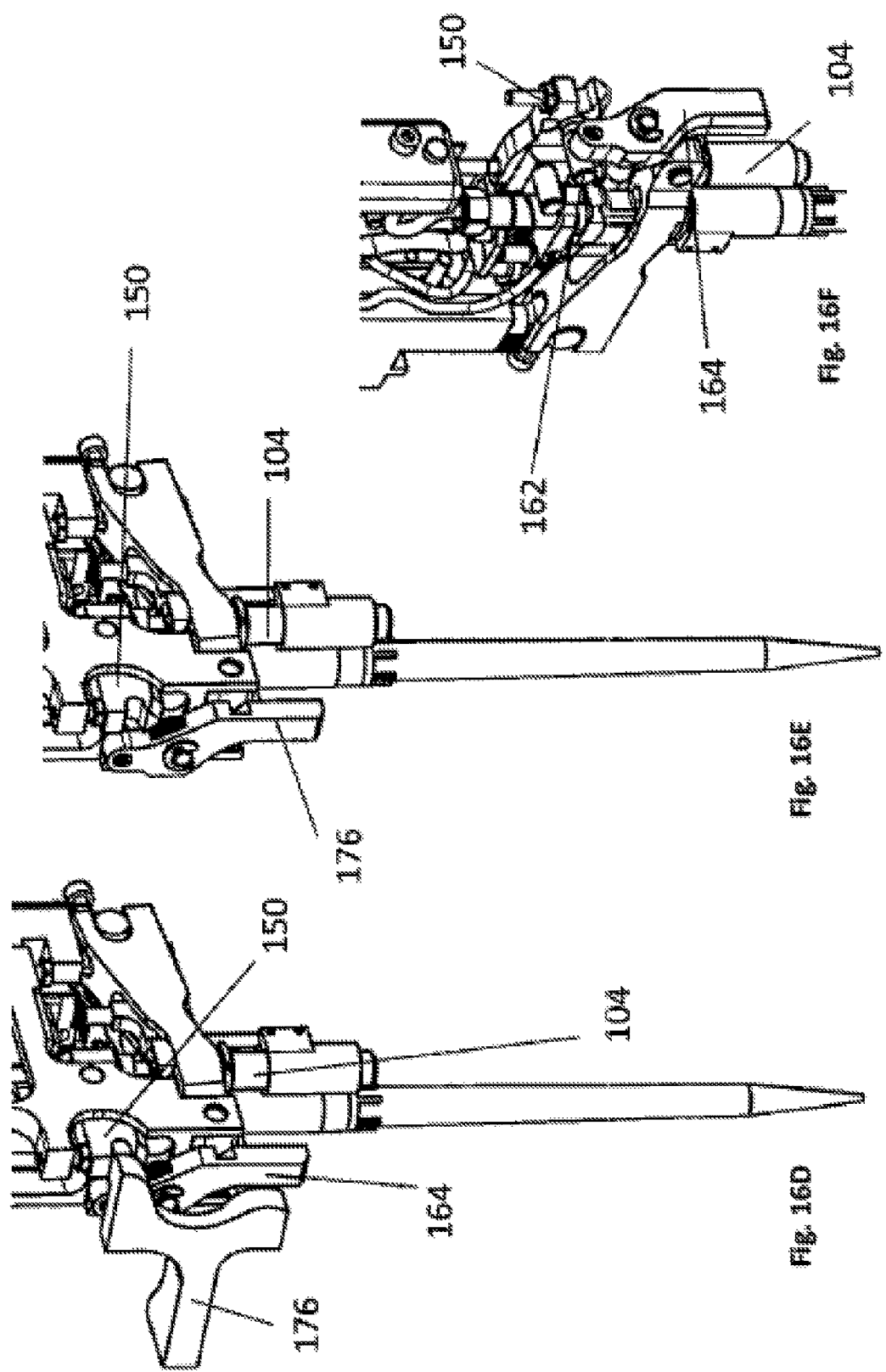

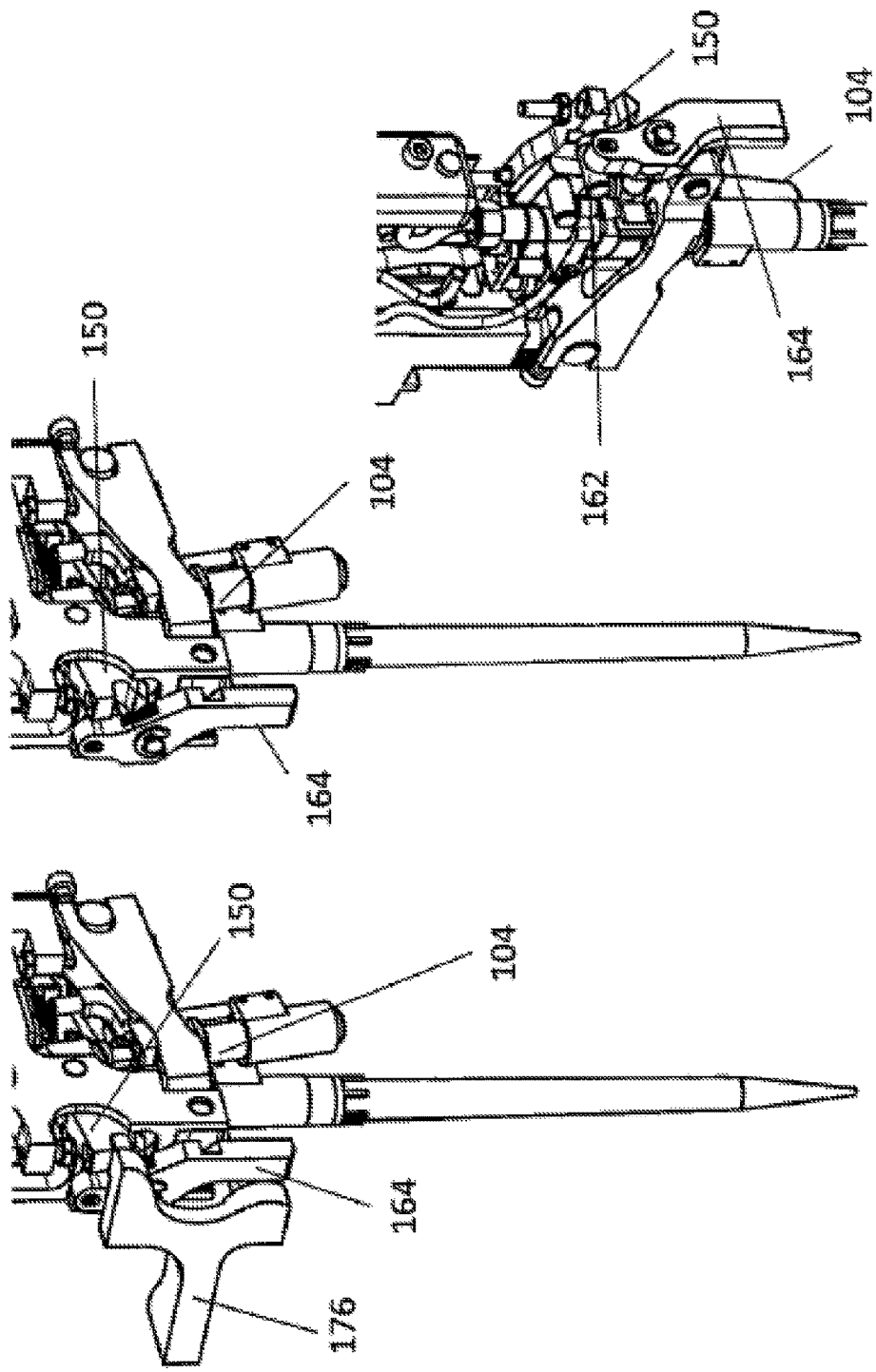

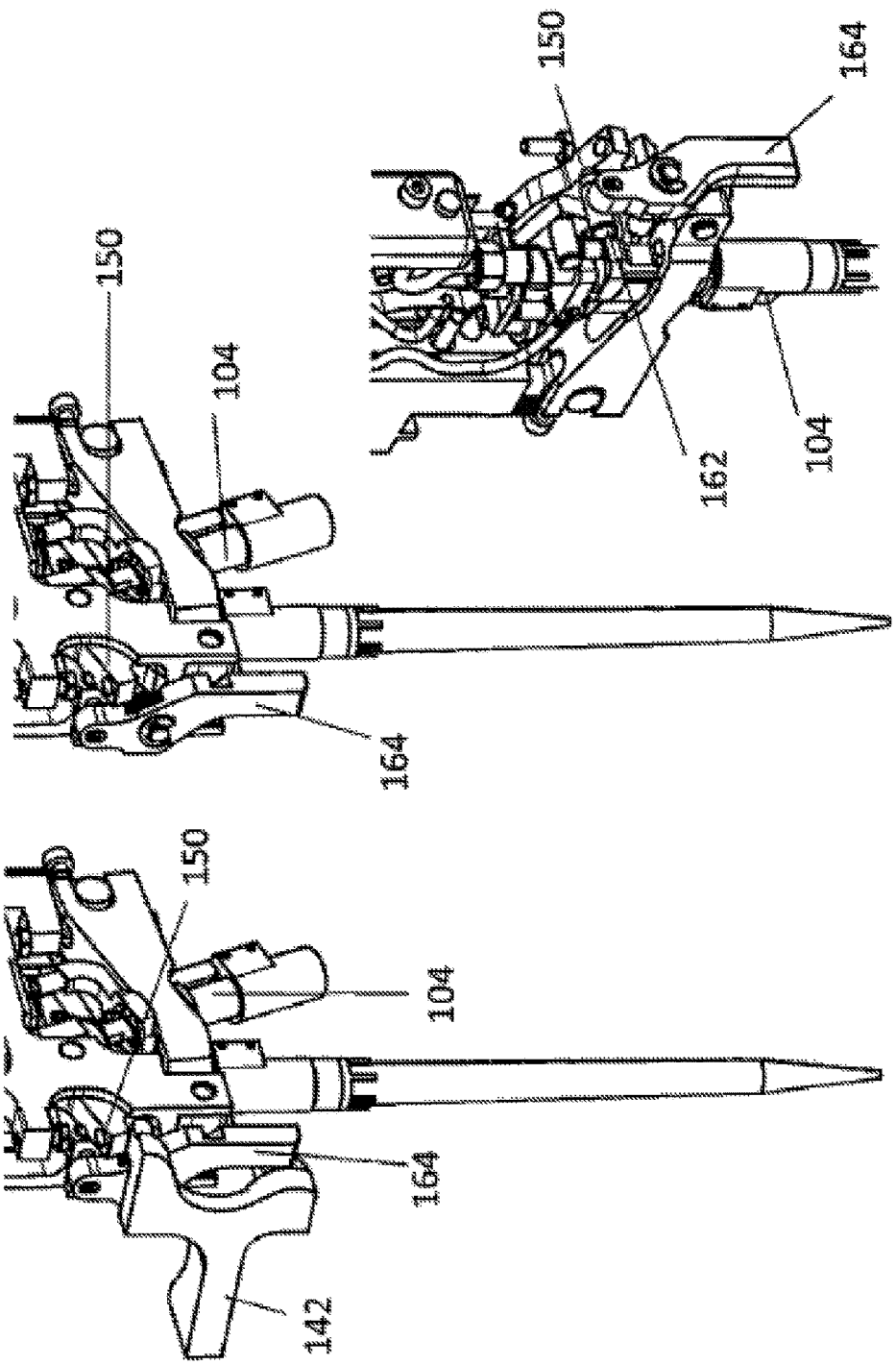

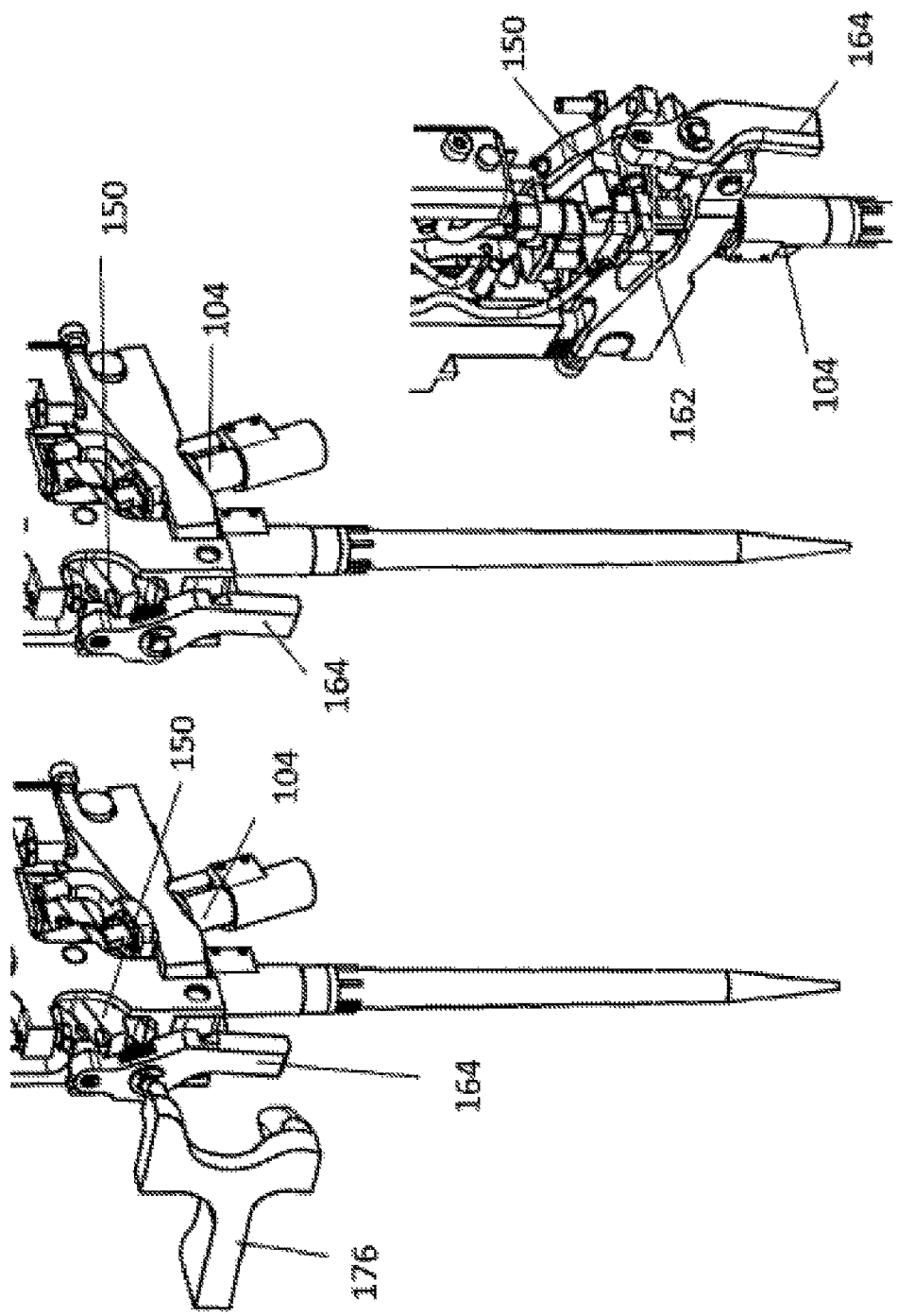

PIPETTING DEVICE FOR AN APPARATUS FOR PROCESSING A SAMPLE OR REAGENT, APPARATUS FOR PROCESSING A SAMPLE OR REAGENT AND METHOD FOR PIPETTING A SAMPLE OR REAGENT

CROSS-REFERENCE TO RELATED APPLICATIONS

This application claims the benefit of priority of EP Application No. 15189536.4, filed Oct. 13, 2015, the disclosure of which is incorporated herein by reference. Reference is also made to EP Application No. 151895933, filed Oct. 13, 2015 (U.S. application Ser. No. 15/291,960, filed Oct. 12, 2016, now U.S. Pat. No. 10,300,480 B2), the disclosure of which is also incorporated herein by reference in its entirety.

FIELD OF THE INVENTION

The present invention relates to a pipetting device for an apparatus for processing a sample or reagent, an apparatus for processing a sample or reagent, and a method for pipetting a sample or reagent.

BACKGROUND OF THE INVENTION

An apparatus for processing a sample or reagent in the sense of the present invention comprises a pipetting device. Such pipetting devices are used for transferring a sample or reagent from a first vessel to a second vessel by means of an aspirating and dispensing operation. Modern apparatus for processing samples of this kind are largely fully automatic in operation and only the samples and/or reagents stored in the vessels have to be inserted into the apparatus and the desired process such as aliquoting or an analysis has to be entered.

The present invention is intended for apparatus such as analytical instruments which operate with liquid samples or reagents which are contained in first vessels. Usually, the samples or reagents stored in the first vessels are withdrawn from the first vessels by pipette probes of a pipettor at the analytical position. Particularly, the pipetting probe of the pipettor is fastened to a moveable arm, dips from above through the open first vessel and an appropriate amount of sample or reagent is sucked in and transferred in the pipette probe, which is also known as transfer needle, to a second vessel. Usually, the first vessels are arranged on a rack in a predetermined pattern. These are handled by multiple automatic pipetting channels of the pipetting device. At the same time, it is required to process either all or just some of the pipetting channels. Multiple pipetting channels working in parallel are disclosed for example in EP 2 410 342 A2.

Using the above described pipetting devices with an analytical instrument provides advantages concerning the parallel handling. Nevertheless, there are still some drawbacks. Particularly, such automatic pipetting devices have an individual control over each pipetting channel which requires much space and many actuators for all individual control mechanisms. Thus, the more pipetting channels are handled by the automatic pipetting device, the more the costs for the pipetting process increase. Further, the space required for the control mechanisms increases due to the increasing number of actuators.

It is therefore an objective of the present invention to provide a pipetting device for an apparatus for processing a sample or reagent, an apparatus for processing a sample or reagent, and a method for pipetting a sample or reagent using such a pipetting device which are improved regarding complexity in the construction and the handling of the samples or reagents. Particularly, there is a desire to provide a pipetting device and an apparatus for processing a sample or reagent with which several pipetting channels may be controlled by using less actuators and space as possibly thereby reducing the costs of the automatic pipetting device.

SUMMARY OF THE INVENTION

This problem is solved by a pipetting device for an apparatus for processing a sample or reagent, an apparatus for processing a sample or reagent and a method for pipetting a sample or a reagent using a pipetting device with the features of the independent claims. Embodiments which might be realized in an isolated fashion or in any arbitrary combination are listed in the dependent claims.

The specification provides a pipetting device for an apparatus for processing a sample or reagent, comprising a coupling mechanism, wherein the coupling mechanism comprises at least a first coupling unit adapted to be coupled to a first pipetting tip and a second coupling unit adapted to be coupled to a second pipetting tip, and a selection element for selectively allowing a coupling of the first coupling unit to or releasing the first coupling unit from the first pipetting tip and for selectively allowing a coupling of the second coupling unit to or releasing the second coupling unit from the second pipetting tip, wherein the selection element is mechanically coupled to the first coupling unit and the second coupling unit.

Also provided is an apparatus for processing a sample or reagent comprising a pipetting device as described herein, an input for a first vessel, said vessel comprising a sample or reagent, and a holder for holding a second vessel to which the sample or reagent is transferrable by the pipetting device.

Moreover, the specification includes a method for pipetting a sample or reagent using a pipetting device as described herein, comprising
 selectively operating the selection element so as to allow the first coupling unit to be coupled to a first pipetting tip,
 selectively operating the selection element so as to allow the second coupling unit to be coupled to a second pipetting tip,
 aspirating a first sample or reagent from a first vessel by means of the first pipetting tip, and/or
 aspirating a second sample or reagent from a second vessel by means of the second pipetting tip.

Additionally, the specification also contemplates a method for pipetting a sample or reagent using a pipetting device as described herein, comprising
 coupling a second pipetting tip to the second coupling unit,
 moving the first coupling unit from the untilted position, in which the first coupling unit and the second coupling unit are arranged parallel to one another, into the tilted position, in which the first coupling unit is tilted relative to the second coupling unit, and
 aspirating a sample or reagent from a first vessel by means of the second pipetting tip while the first coupling unit is in the tilted position.

Thus, the disclosure provides a first embodiment including a pipetting device for an apparatus for processing a sample or reagent, comprising a coupling mechanism, wherein the coupling mechanism comprises at least a first coupling unit adapted to be coupled to a first pipetting tip and a second coupling unit adapted to be coupled to a second pipetting tip, and a selection element for selectively allowing a coupling of the first coupling unit to or releasing the first coupling unit from the first pipetting tip and for selectively allowing a coupling of the second coupling unit to or releasing the second coupling unit from the second pipetting tip, wherein the selection element is mechanically coupled to the first coupling unit and the second coupling unit.

In the first embodiment, the coupling mechanism further comprises a first coupling lever connected to the first coupling unit and a second coupling lever connected to the second coupling unit, wherein the first coupling lever is moveable between an engagement position, in which the first coupling unit is adapted to be coupled to the first pipetting tip, and a release position, in which the first coupling unit is adapted to be released from first pipetting tip, wherein the second coupling lever is moveable between an engagement position, in which the second coupling unit is adapted to be coupled to the second pipetting tip, and a release position, in which the second coupling unit is adapted to be released from second pipetting tip, wherein the selection element is operatively coupled to the first coupling lever and the second coupling lever. The selection element can include a rotatory disc, wherein the rotatory disc comprises a protrusion and a lowered portion adapted to selectively engage none, one or both of the first coupling lever and the second coupling lever.

In addition, the first coupling lever is in the engagement position when engaged by the protrusion and is in the release position when engaged by the lowered portion, wherein the second coupling lever is in the engagement position when engaged by the protrusion and is in the release position when engaged by the lowered portion. Still further, the rotatory disc can be rotatable such that the protrusion and the lowered portion are each adapted to selectively engage none, one or both of the first coupling lever and the second coupling lever. The rotatory disc can be disposed on a rotatable shaft adapted to rotate the rotatory disc. Still further, the first embodiment can include a motor adapted to rotate the shaft.

The first embodiment provide a pipetting device in which the first coupling unit comprises a first prestress member adapted to axially prestress a first axial stop with respect to a first counter-stop located on a first inner surface of the first pipetting tip, wherein the second coupling unit comprises a second prestress member adapted to axially prestress a second axial stop with respect to a second counter-stop located on a second inner surface of the second pipetting tip. The first prestress member can include a first elastically deformable sealing member adapted to seal off the first pipetting tip with respect to the first coupling unit, wherein the second prestress member comprises a second elastically deformable sealing member adapted to seal off the second pipetting tip with respect to the second coupling unit. Moreover, the first coupling unit comprises a first squeezing device adapted to axially compress the first sealing member, wherein the second coupling unit comprises a second squeezing device adapted to axially compress the second sealing member. The first sealing member can be in an axially uncompressed state substantially not in a prestress force producing engagement with the first inner surface of the first pipetting tip, and is adapted to enter into a prestress force producing engagement with the first inner surface of the first pipetting tip in the course of an axial compressing, wherein the second sealing member is in an axially uncompressed state substantially not in a prestress force producing engagement with the second inner surface of the second pipetting tip, and is adapted to enter into a prestress force producing engagement with the second inner surface of the second pipetting tip in the course of an axial compressing. Still further, the first squeezing device is operatively coupled to the first coupling lever, wherein the second squeezing device is operatively coupled to the second coupling lever.

Additionally, the pipetting device of the first embodiment can comprise a first syringe and a second syringe, wherein the first syringe comprises a first plunger and the second syringe comprises a second plunger, and one single actuator adapted to operate the first plunger and the second plunger. The first syringe and the second syringe can be arranged parallel to one another and optionally, the first syringe and the second syringe extend into the coupling mechanism.

Still further, in the first embodiment the device further includes a tilt mechanism for moving the first coupling unit between an untilted position, in which the first coupling unit and the second coupling unit are arranged parallel to one another, and a tilted position, in which the first coupling unit is tilted relative to the second coupling unit. In this embodiment, the tilt mechanism is tiltable around a first pivot. The device can also include a tilt mechanism trigger adapted to trigger the tilt mechanism. The tilt mechanism trigger can be adapted to releasably fix the tilt mechanism in the untilted position. The tilt mechanism mechanism can comprise a first recess and the tilt mechanism trigger comprises a pin, wherein the tilt mechanism is fixable in the untilted position by means of an engagement of the pin with the first recess. Still further, the tilt mechanism trigger can include a trigger lever adapted to pivot around a second pivot. The pin can be connected to the trigger lever, and optionally, the tilt mechanism is releasable from the untilted position by means of a disengagement of the pin from the first recess. The pin can also be selectively engageable with and disengageable from the first recess by means of pivoting the trigger lever around the second pivot. The tilt mechanism can be releasably fixable in the tilted position.

In the first embodiment, the coupling mechanism can further comprise a first coupling unit protrusion disposed on the first coupling unit, wherein the first coupling lever comprises a first coupling lever recess, wherein the tilt mechanism is releasably fixable in the tilted position by means of engagement of the first coupling unit protrusion with the first coupling lever recess. The tilt mechanism can be releasable from the tilted position by means of disengagement of the first coupling unit protrusion from the first coupling lever recess. The first coupling unit protrusion can be selectively engageable with and disengageable from the first coupling lever recess by means of pivoting the tilt mechanism around the first pivot. Still further, the tilt mechanism trigger can be adapted to be activated by means of engagement with an activation device of the analytical device, for example, the tilt mechanism trigger is adapted to be activated by means of a movement of the pipetting device relative to the activation device in a first direction. In a specific embodiment, the tilt mechanism comprises a second recess engageable with a protrusion of the activation device, wherein the tilt mechanism is tiltable around the first pivot by means of a movement of the pipetting device relative to the activation device in a second direction with the second recess engaged with the protrusion of the activation device. The second direction can be different from the first direction, e.g., the second direction is perpendicular to the first direction. The tilt mechanism can be tiltable around the first pivot by means of an actuator.

The first embodiment can further include a sensor for detection whether the first coupling unit is in the untilted position or the tilted position, e.g., a Hall sensor. The device can also include a magnet arranged at the tilt mechanism.

A second embodiment of the disclosure is an apparatus for processing a sample or reagent comprising a pipetting device as described herein, an input for a first vessel, said vessel comprising a sample or reagent, and a holder for holding a second vessel to which the sample or reagent is transferrable by the pipetting device.

A third embodiment of the disclosure is a method for pipetting a sample or reagent using a pipetting device as described herein, comprising
- selectively operating the selection element so as to allow the first coupling unit to be coupled to a first pipetting tip,
- selectively operating the selection element so as to allow the second coupling unit to be coupled to a second pipetting tip,
- aspirating a first sample or reagent from a first vessel by means of the first pipetting tip, and/or
- aspirating a second sample or reagent from a second vessel by means of the second pipetting tip.

Finally, the disclosure also provides a method for pipetting a sample or reagent using a pipetting device as described herein, comprising
- coupling a second pipetting tip to the second coupling unit,
- moving the first coupling unit from the untilted position, in which the first coupling unit and the second coupling unit are arranged parallel to one another, into the tilted position, in which the first coupling unit is tilted relative to the second coupling unit, and
- aspirating a sample or reagent from a first vessel by means of the second pipetting tip while the first coupling unit is in the tilted position.

BRIEF DESCRIPTION OF THE FIGURES

Further features and embodiments of the invention will be disclosed in more detail in the subsequent description of embodiments. Therein, the respective features may be realized in an isolated fashion as in any arbitrary feasible combination, as a skilled person will realize. The scope of the invention is not restricted by the disclosed embodiments. The embodiments are schematically depicted in the figures. Therein, identical reference numbers in these figures refer to identical or functionally comparable elements.

FIG. 4 shows a perspective view of the pipetting device in a first operation state.

FIG. 5 shows a perspective view of the pipetting device in a second operation state.

FIG. 8 shows a left side perspective view of a pipetting device according to the present invention.

FIG. 9A shows another left side perspective view of the pipetting device 100 and FIG. 9B shows an expanded view of a holder 202 for holding a second vessel 204 to which the sample or reagent is transferrable by means of the pipetting device 100 depicted in FIG. 9A.

FIG. 14 shows a schematic illustration of an apparatus for processing a sample or reagent.

FIGS. 15A-15I show a second embodiment of a selection element as the components of the device are moved. In FIG. 15A, the first and second connection members are both located in the central recess. From this position, the linear shifting block can move either to the right, such that the coupling lever is moved to the lowered position in FIG. 15B, and further moved to the right such that both coupling levers are moved to the lowered position in FIG. 15C, and further movement to the right allows to select coupling lever to be in the lowered position, while coupling lever is not (FIG. 15D). With a further movement of the linear shifting block, none of the coupling levers is selected to be in the lowered position (FIG. 15E). FIGS. 15F-15I show the movement of the linear shifting block in the opposite direction, allowing to selectively move either coupling lever (FIG. 15F), both coupling levers (FIG. 15G), coupling lever (FIG. 15H), or none of the coupling levers (FIG. 15I) into the lowered position.

FIGS. 16A-16O show a detailed view of the tilt mechanism and the progression of the elements of the tilt mechanism from the untilted to the tilted position. FIG. 16A shows the trigger lever position when the coupling unit is in the untilted position and pin is in the locked position. When the pin 162 is in the locked position, the tilt mechanism 150 cannot be moved. FIG. 16B corresponds to FIG. 16A, except that the activation device was removed from the drawing to better show the mechanism. FIG. 16C shows a close-up from the left side of the pipetting device shown in FIGS. 16(a) and 16(b) with the trigger lever, first coupling unit and tilt mechanism in the unactivated position and pin in the locked position. FIG. 16D shows the activation of the trigger lever by the activation device. FIG. 16E corresponds to FIG. 16D, except that the activation device was removed from the drawing to better show the mechanism. FIG. 16F shows a close-up from the left side of the pipetting device shown in FIGS. 16D and 16E with the trigger lever moved counterclockwise, first coupling unit still in the untilted position, pin in the unlocked position and tilt mechanism in the unactivated position. FIG. 16G shows the device after movement of the tilt mechanism and first coupling unit when the activation device is moved downwards relative to the trigger lever. FIG. 16H corresponds to FIG. 16G, except that the activation device was removed from the drawing to better show the mechanism. FIG. 16I shows a close-up from the left side of the pipetting device shown in FIGS. 16G and 16H, where the tilt mechanism is in a lower position compared to the previous states, and first coupling unit is partly tilted. FIG. 16J shows the device after movement of the first coupling unit into the final tilt position. FIG. 16K corresponds to FIG. 16J, except that the activation device was removed from the drawing to better show the mechanism. FIG. 16L shows a close-up from the left side of the pipetting device shown in FIGS. 16K and 16J, where the tilt mechanism is in a lower position compared to FIG. 16I, and first coupling unit is fully tilted. FIG. 16M shows the tilted pipetting device after removal of the activation device. FIG. 16N corresponds to FIG. 16M, except that the activation device was removed from the drawing to better show the mechanism. FIG. 16O shows a close-up from the left side of the pipetting device shown in FIGS. 16M and 16N, where the trigger lever is slightly moved clockwise, compared to FIG. 16I.

DETAILED DESCRIPTION OF THE INVENTION

Figure 1:
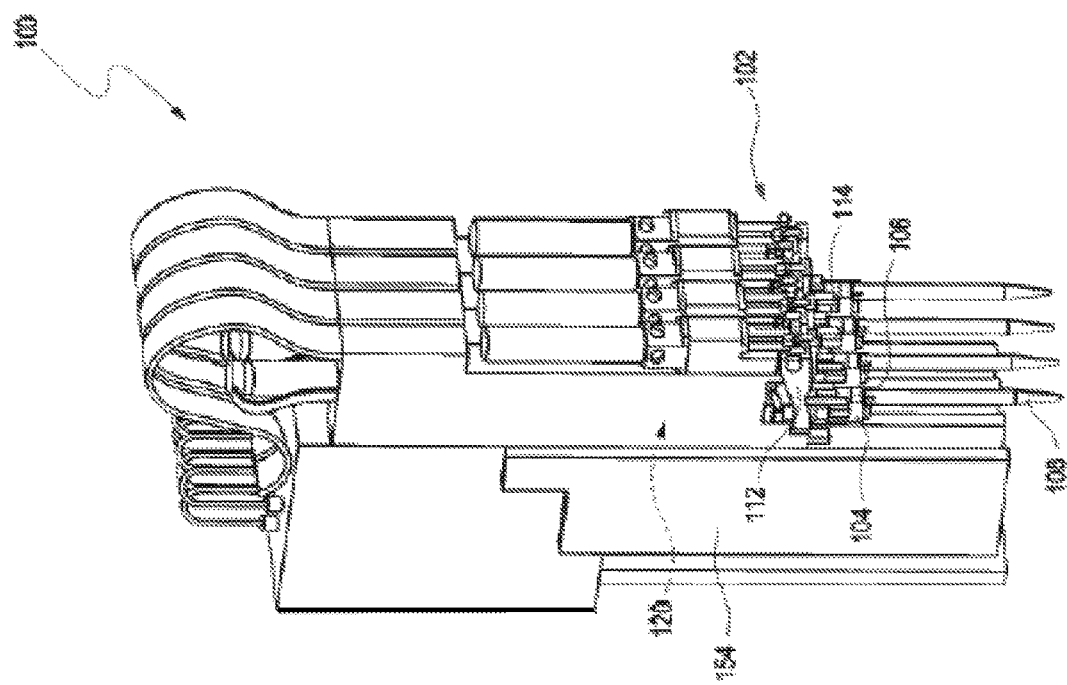
FIG. 1 shows a perspective view of a pipetting device according to the present invention.

According to the present invention, a pipetting device for an apparatus for processing a sample or reagent is disclosed. The pipetting device comprises a coupling mechanism, wherein the coupling mechanism comprises at least a first coupling unit adapted to be coupled to a first pipetting tip and a second coupling unit adapted to be coupled to a second pipetting tip, and a selection element for selectively allowing a coupling of the first coupling unit to or releasing the first coupling unit from the first pipetting tip and for selectively allowing a coupling of the second coupling unit to or releasing the second coupling unit from the second pipetting tip, wherein the selection element is not only operatively but also mechanically coupled to the first coupling unit and the second coupling unit. Thus, it is possible to attach either one or the other pipetting tip or both or none on the coupling mechanism which may be operated by a single constructional member. The term "mechanically coupled" in the sense of the present invention is to be understood as a direct or indirect connection or coupling of the selection element to the first coupling unit and the second coupling unit. The connection or coupling may be realized by a non-positive connection, positive connection and/or adhesive bond.

The term "sample", as used herein, refers to a material suspected of containing an analyte of interest. The sample can be derived from any biological source, such as a physiological fluid, including, blood, saliva, ocular lens fluid, cerebral spinal fluid, sweat, urine, milk, ascites fluid, mucous, synovial fluid, peritoneal fluid, amniotic fluid, tissue, cells or the like. The test sample can be pretreated prior to use, such as preparing plasma from blood, diluting viscous fluids, lysis or the like; methods of treatment can involve filtration, distillation, concentration, inactivation of interfering components, and the addition of reagents. A sample may be used directly as obtained from the source or following a pretreatment to modify the character of the sample, e.g. after being diluted with another solution or after having being mixed with reagents e.g. to carry out one or more diagnostic assays like e.g. clinical chemistry assays, immunoassays, coagulation assays, nucleic acid testing, etc. The term "sample" as used herein is therefore not only used for the original sample but also relates to a sample which has already been processed (pipetted, diluted, mixed with reagents, enriched, having been purified, having been amplified etc.). As used herein, the term "analyte" refers to the compound or composition to be detected or measured.

The term "reagent" is used to indicate a composition required for treatment of a sample. Reagents may be any liquid, e.g. a solvent or chemical solution, which needs to be mixed with a sample and/or other reagent in order e.g. for a reaction to occur, or to enable detection. A reagent may be for example a diluting liquid, including water, it may comprise an organic solvent, it may comprise a detergent, it may be a buffer. Reagents may also be dry reagents adapted e.g. to be dissolved by a sample, another reagent or a diluting liquid. A reagent in the more strict sense of the term may be a liquid solution containing a reactant, typically a compound or agent capable e.g. of binding to or chemically transforming one or more analytes present in a sample. Examples of reactants are enzymes, enzyme substrates, conjugated dyes, protein-binding molecules, nucleic acid binding molecules, antibodies, chelating agents, promoters, inhibitors, epitopes, antigens, etc.

The term "processing a sample or reagent" may relate to transferring, aliquoting, isolating, purifying, incubating, treating or reacting a sample or reagent or combining a reagent with a sample.

It is to be noted that the terms "first" and "second" are exclusively used with the present invention to conceptually distinguish between the respective constructional members and are not intended to indicate any order of importance or the like.

The term "pipetting tip" as used with the present invention covers disposable pipetting tips, which may be used only with a single pipetting process, and reusable pipetting tips, which may be used with more than one pipetting process. Disposable pipetting tips are usually made of plastics and are disposed after the pipetting process. Reusable pipetting tips may be designed as pipetting needles and are usually made of metal or any other material suitable for use with the respective samples. Accordingly, the term "coupled to" as used with the present invention in connection with the coupling of a pipetting tip to a coupling unit covers a releasable coupling process of a pipetting tip to a coupling unit as well as a permanent coupling of the pipetting tip to the coupling unit. Regarding the latter case, a pipetting needle may be permanently coupled such as screwed to the coupling unit except for an exchange caused by damage or for maintenance purposes.

Pipetting devices with coupling units are well known in the art. Suitable coupling mechanisms include coupling units which comprise a coupling element which is expandable. This ensures that when the coupling unit is inserted into the pipette tip, it does not immediately couple the pipette tip (e.g. by friction). Without expanding the coupling element, the coupling unit can be withdrawn again from the pipette tip without the pipette tip being coupled. This allows for the selective coupling of the pipette tip to the coupling unit by expanding the coupling element using a selection element. This also allows for selective release of the pipette tip from the coupling unit by reversing the expansion of the coupling element using a selection element.

One type of coupling mechanism is described in EP1171240, the disclosure of which is incorporated herein by reference. This coupling mechanism comprises a compressed O-Ring as expandable coupling element positioned in the coupling unit, and a recess in the pipette tip interface region. The coupling unit is moved into the interface region of the pipette tip, and the compressed O-Ring is expanded into the recess area of the pipette tip interface region to couple the coupling unit and the pipette tip.

Another embodiment of a suitable coupling mechanism is described in US20100196210, the disclosure of which is incorporated herein by reference. The coupling mechanism comprises a separate sealing element (e.g. an O-Ring, but other structures are also proposed) and a holding element which is expandable and interacts with a recess on the pipette tip interface or an undercut to couple the coupling unit to the pipette tip interface.

In one embodiment, the pipetting device may comprise at least two pairs of first and second coupling units, wherein the status of coupling between a first coupling unit and a first pipette tip of one pair is the same as the status of coupling between a first coupling unit and a first pipette tip of another pair, and the status of coupling between second coupling unit and second pipette tip of one pair is the same as the status of coupling between a second coupling unit and a second pipette tip of another pair.

The coupling mechanism may further comprise a first coupling lever connected to the first coupling unit and a second coupling lever connected to the second coupling unit, wherein the first coupling lever is moveable between an engagement position, in which the first coupling unit is adapted to be coupled to the first pipetting tip, and a release position, in which the first coupling unit is adapted to be released from the first pipetting tip, wherein the second coupling lever is moveable between an engagement position, in which the second coupling unit is adapted to be coupled to the second pipetting tip, and a release position, in which the second coupling unit is adapted to be released from the second pipetting tip, wherein the selection element is operatively coupled to the first coupling lever and the second coupling lever. Thus, the construction of well-established coupling levers does not have to be modified but may be used with the selection element of the present invention.

The selection element may comprise a rotatory disc, wherein the rotatory disc comprises a protrusion and a lowered portion adapted to selectively engage none, one or both of the first coupling lever and the second coupling lever. A rotatory disc in the sense of the present invention is to be understood as a disc which is rotatable. Thus, the protrusion may engage none, one or both of the first coupling lever and the second coupling lever. Also the lowered portion may engage none, one or both of the first coupling lever and the second coupling lever. Needless to say, the protrusion and the lowered portion may not simultaneously engage the first coupling lever and the second coupling lever but only the protrusion or the lowered portion may simultaneously engage the first coupling lever and the second coupling lever. However, it is possible that the protrusion engages one of the first coupling lever and the second coupling lever while the lowered portion engages the other one of the first coupling lever and the second coupling lever. Further, if one of the protrusion and the lowered portion engages both of the first coupling lever and the second coupling lever, then the other one of the protrusion and the lowered portion is disengaged from the first coupling lever and the second coupling lever. Thus, with a single rotatory disc having this specific design it is possible to provide a significant amount of flexibility regarding the engagement possibilities of the first coupling lever and the second coupling lever.

In another embodiment, instead of the rotatory disk, the selection element may comprise a linear shifting block which comprises protrusions in the bottom surface adapted to selectively engage none, one or both of the first coupling lever and the second coupling lever. In one embodiment, a central recess is located between two protrusions on the bottom surface of the shifting block. This permits the rapid selection of either the right or the left coupling lever to move into the lowered position.

The first coupling lever may be in the engagement position when engaged by the protrusion and may be in the release position when engaged by the lowered portion, wherein the second coupling lever may be in the engagement position when engaged by the protrusion and may be in the release position when engaged by the lowered portion. Thus, engagement and disengagement of the first coupling lever and the second coupling lever is realized by the rotational position of the rotatory disc.

The rotatory disc may be rotatable such that the protrusion and the lowered portion are each adapted to selectively engage none, one or both of the first coupling lever and the second coupling lever. Thus, by rotating the rotatory disc it is possible to realize the engagement or disengagement operation.

The rotatory disc may be disposed on a rotatable shaft adapted to rotate the rotatory disc. Thus, the rotatory disc may be rotated by means of a rather simple construction.

The pipetting device may further comprise a motor adapted to rotate the shaft. Thus, the need for a manual operation of the rotatory disc is omitted.

The first coupling unit may comprise a first prestress member adapted to axially prestress a first axial stop with respect to a first counter-stop located on a first inner surface of the first pipetting tip, wherein the second coupling unit may comprise a second prestress member adapted to axially prestress a second axial stop with respect to a second counter-stop located on a second inner surface of the second pipetting tip. Thus, the first pipetting tip and the second pipetting tip may be reliably and releasably fixed to the first coupling unit and the second coupling unit.

The first prestress member may comprise a first elastically deformable sealing member adapted to seal off the first pipetting tip with respect to the first coupling unit, wherein the second prestress member may comprise a second elastically deformable sealing member adapted to seal off the second pipetting tip with respect to the second coupling unit. Thus, the samples in the pipetting tips may be sealed off the surroundings in order to avoid a deterioration or contamination of the sample.

The first coupling unit may comprise a first squeezing device adapted to axially compress the first sealing member, wherein the second coupling unit may comprise a second squeezing device adapted to axially compress the second sealing member. The first sealing member may be in an axially uncompressed state substantially not in a prestress force producing engagement with the first inner surface of the first pipetting tip, and may be adapted to enter into a prestress force producing engagement with the first inner surface of the first pipetting tip in the course of an axial compressing, wherein the second sealing member may be in an axially uncompressed state substantially not in a prestress force producing engagement with the second inner surface of the second pipetting tip, and may be adapted to enter into a prestress force producing engagement with the second inner surface of the second pipetting tip in the course of an axial compressing. Thus, by means of engagement of the first sealing member and the second sealing member the first pipetting tip and the second pipetting tip may be reliably and releasably fixed to the first coupling unit and the second coupling unit.

The first squeezing device may be operatively coupled to the first coupling lever, wherein the second squeezing device may be operatively coupled to the second coupling lever. Thus, the first squeezing device may be operated by the first coupling lever and the second squeezing device may be operated by the second coupling lever.

The pipetting device may further comprise a first syringe and a second syringe, wherein the first syringe comprises a first plunger and the second syringe comprises a second plunger, and one single actuator adapted to operate the first plunger and the second plunger. Thus, the first plunger and the second plunger may be operated by a single actuator. Thus, it is not necessary to associate a single plunger with a single actuator but the number of actuators necessary for operating more than one plunger is reduced.

The first syringe and the second syringe may be arranged parallel to one another. Thus, the construction for the operation of the plungers by means of a single actuator may be simplified.

The first syringe and the second syringe may extend into the coupling mechanism. Thus, a compact construction is provided.

The pipetting device may further comprise a tilt mechanism for moving the first coupling unit between an untilted position, in which the first coupling unit and the second coupling unit are arranged parallel to one another, and a tilted position, in which the first coupling unit is tilted relative to the second coupling unit. Thus, according to the pipetting device of the present invention, the first coupling unit may be moved away from the second coupling unit by means of the pivotal movement. Thereby, a pipetting tip coupled to the second coupling unit may be immersed deeper into a sample vessel as the first coupling unit does not obstruct an immersion movement of the second coupling unit if tilted relative to the second coupling unit.

The tilt mechanism may be tiltable around a first pivot. Thus, tilt mechanism is also moved in a tilted position by means of a single pivotal movement around a single pivotal or rotational axis which represents a rather simple construction.

The pipetting device may further comprise a tilt mechanism trigger adapted to trigger the tilt mechanism. Thus, the tilting of the first coupling unit must first be initiated or triggered before the first coupling unit is tilted.

The tilt mechanism trigger may be adapted to releasably fix the tilt mechanism in the untilted position. Thus, an unwanted tilting of the first coupling unit is prevented.

The tilt mechanism may comprise a first recess and the tilt mechanism trigger may comprise a pin, wherein the tilt mechanism is fixable in the untilted position by means of an engagement of the pin with the first recess. Thus, an unwanted tilting of the first coupling unit is prevented by means of the engagement of the pin with the first recess.

The tilt mechanism trigger may comprise a trigger lever adapted to pivot around a second pivot. Thus, the tilting movement of the tilt mechanism and the first coupling unit may be initiated or triggered by means of a simple rotational or pivotal movement of the trigger lever.

The pin may be connected to the trigger lever. Thus, the pin may be moved by means of a movement of the trigger lever.

The tilt mechanism may be releasable from the untilted position by means of a disengagement of the pin from the first recess. Thus, while the tilt mechanism may be safely fixed in the untilted position of the first coupling unit, it may be released therefrom by means of a simple movement of the pin out of the first recess.

The pin may be selectively engageable with and disengageable from the first recess by means of pivoting the trigger lever around the second pivot. Thus, while the tilt mechanism may be safely fixed in the untilted position of the first coupling unit, it may be released therefrom by means of a simple pivotal movement of the trigger lever which causes the pin to move out of the first recess.

The tilt mechanism may be releasably fixable in the tilted position. Thus, an unwanted movement back into the untilted position of the first coupling unit and a collision with a sample vessel by the first coupling unit may be prevented.

The coupling mechanism may further comprise a first coupling lever connected to the first coupling unit, a second coupling lever connected to the second coupling unit, and a first coupling unit protrusion disposed on the first coupling unit. The first coupling lever may comprises a first coupling lever recess. The tilt mechanism may be releasably fixable in the tilted position by means of engagement of the first coupling unit protrusion with the first coupling lever recess. Thus, an unwanted movement back into the untilted position of the first coupling unit and a collision with a sample vessel by the first coupling unit may be reliably prevented by means of a rather simple construction.

The tilt mechanism may be releasable from the tilted position by means of disengagement of the first coupling unit protrusion from the first coupling lever recess. Thus, by means of a movement of the first coupling unit protrusion out of the first coupling lever recess, the first coupling unit may be moved back into the untilted position.

The first coupling unit protrusion may be selectively engageable with and disengageable from the first coupling lever recess by means of pivoting the tilt mechanism around the first pivot. Thus, by means of a rotational or pivotal movement of the first coupling unit protrusion into or out of the first coupling lever recess, the first coupling unit may be moved into the tilted position or the untilted position.

The tilt mechanism trigger may be adapted to be activated by means of engagement with an activation device of the analytical device. Thus, the tilt mechanism trigger may be activated by means of a device external to or separate from the pipetting device. This avoids the necessity to provide the pipetting device with an actuator for activating the tilt mechanism trigger.

The tilt mechanism trigger may be adapted to be activated by means of a movement of the pipetting device relative to the activation device in a first direction. Thus, by means of a movement of the pipetting device, which may be easily controlled, the tilt mechanism may be activated.

The tilt mechanism may comprise a second recess engageable with a protrusion of the activation device. The tilt mechanism may be tiltable around the first pivot by means of a movement of the pipetting device relative to the activation device in a second direction with the second recess engaged with the protrusion of the activation device. The second direction may be different from the first direction. Thus, the tilt mechanism may be tilted by means of a device external to or separate from the pipetting device. This avoids the necessity to provide the pipetting device itself with an actuator for tilting the tilt mechanism and the first coupling unit.

The second direction may be perpendicular to the first direction. Thus, by means of a movement of the pipetting device, the tilt mechanism may not only be triggered but also be tilted.

The tilt mechanism may be tiltable around the first pivot by means of an actuator. Thus, an alternative is realized which may be realized if it is desired to omit the actuation device.

The pipetting device may further comprise a sensor for detection whether the first coupling unit is in the untilted position or the tilted position. The sensor may be a Hall sensor. The pipetting device may further comprise a magnet arranged at the tilt mechanism. Thus, it may be detected whether the first coupling unit is in the untilted position or the tilted position. This ensures that the second pipetting device is immersed in a sample vessel only if a collision of the first coupling unit and the sample vessel may not occur.

According to the present invention, an apparatus for processing a sample or reagent is disclosed. The apparatus comprises a pipetting device as described before, an input for a first vessel, wherein the vessel comprises a sample or reagent, a holder for holding a second vessel to which the sample or reagent is transferrable by means of the pipetting device.

According to the present invention, a method for pipetting a sample or a reagent using a pipetting device as described before is disclosed. The method comprises:

selectively operating the selection element so as to allow the first coupling unit to be coupled to a first pipetting tip, selectively operating the selection element so as to allow the second coupling unit to be coupled to a second pipetting tip, aspirating a first sample or reagent from a first vessel by means of the first pipetting tip, and/or aspirating a second sample or reagent from a second vessel by means of the second pipetting tip.

According to the present invention, a method for pipetting a sample or a reagent using a pipetting device as described before is disclosed. The method comprises coupling a second pipetting tip to the second coupling unit, moving the first coupling unit from the untilted position, in which the first coupling unit and the second coupling unit are arranged parallel to one another, into the tilted position, in which the first coupling unit is tilted relative to the second coupling unit, and aspirating a sample or reagent from a first vessel by means of the second pipetting tip while the first coupling unit is in the tilted position.

FIG. 1 shows a perspective view of a pipetting device 100. The pipetting device 100 may be designed as a so-called pipettor. The pipetting device 100 comprises a coupling mechanism 102. The coupling mechanism 102 comprises at least a first coupling unit 104 and a second coupling unit 106. The first coupling unit 104 is adapted to be coupled to a first pipetting tip 108. The second coupling unit 106 is adapted to be coupled to a second pipetting tip 110. The coupling mechanism 102 further comprises a first coupling lever 112 which is connected to the first coupling unit 104. The coupling mechanism 102 further comprises a second coupling lever 114 which is connected to the second coupling unit 106. The first coupling lever 112 is movable between an engagement position, in which the first coupling unit 104 is adapted to be coupled to the first pipetting tip 108 and a release position, in which the first coupling unit 104 is adapted to be released from the first pipetting tip 108. Analogously, the second coupling lever 114 is movable between an engagement position, in which the second coupling unit 106 is adapted to be coupled to the second pipetting tip 110, and a release position, in which the second coupling unit 106 is adapted to be released from the second pipetting tip 110. For this purpose, the first coupling unit 106 comprises a first prestress member (not shown in detail) adapted to axially prestress the first axial stop with respect to a first counter-stop located on the first inner surface of the first pipetting tip 108. The second coupling unit 106 comprises a second prestress member (not shown in detail) adapted to axially prestress a second axial stop with respect to a second counter-stop located on a second inner surface of the second pipetting tip 110. The first prestress member comprises a first elastically deformable sealing member adapted to seal off the first pipetting tip 108 with respect to the first coupling unit 104. The second prestress member comprises a second elastically deformable sealing member adapted to seal off the second pipetting tip 110 with respect to the second coupling unit 106.

The first coupling unit 104 comprises a first squeezing device 116 adapted to axially compress the first sealing member. The second coupling unit 106 comprises a second squeezing device adapted to axially compress the second sealing member. The first sealing member is in an axially compressed state substantially not in a prestressed force producing engagement with the first inner surface of the first pipetting tip 108, and is adapted to enter into a prestress force producing engagement with the first inner surface of the first pipetting tip 108 in the course of an axial compressing. The second sealing is in an axially uncompressed state substantially not in a prestressed force producing engagement with a second inner surface of the second pipetting tip 110, and is adapted to enter into a prestress force producing engagement with a second inner surface of the second pipetting tip 110 in the course of an axial compressing. As can be taken from FIGS. 1-3, the first squeezing device 116 is operatively coupled to the first coupling lever 112. The second squeezing device 118 is operatively coupled to the second coupling lever 114.

Figure 2:
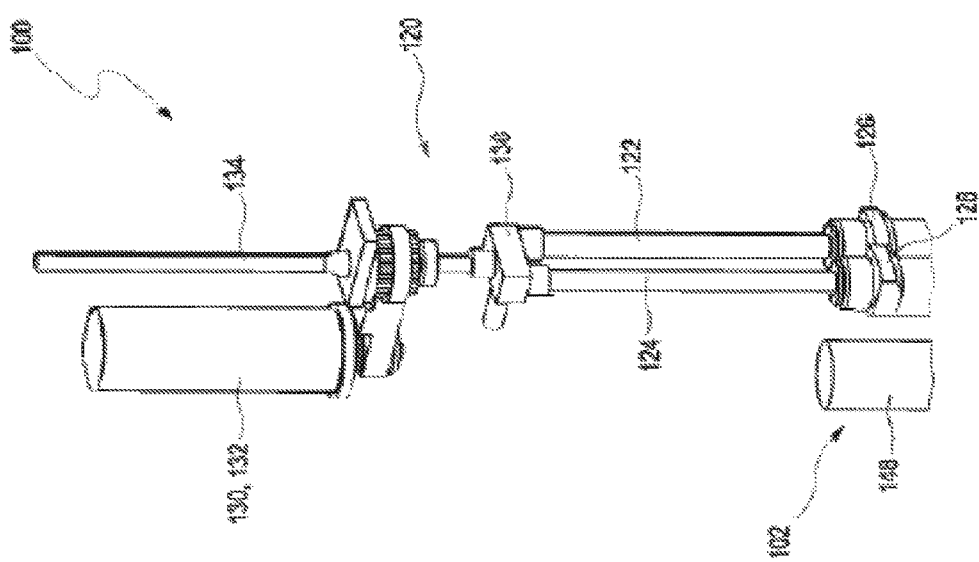
FIG. 2 shows a perspective view of a pipetting mechanism of the pipetting device.

FIG. 2 shows a perspective view of a pipetting mechanism 120 of the pipetting device 100. The pipetting mechanism 120 comprises a first syringe 122 and a second syringe 124. The first syringe 122 comprises a first plunger 126. The second syringe 124 comprises a second plunger 128. The pipetting mechanism 120 further comprises one single actuator 130 adapted to operate the first plunger 126 and the second plunger 128. For example, the actuator 130 is formed as a motor 132 adapted to drive a spindle 134. The spindle 134 is connected to the first plunger 126 and the second plunger 128 by means of a connector 136. Thus, by axially moving the spindle 134 by means of the motor 132, the first plunger 126 and the second plunger 128 simultaneously move in an axial direction. Further, the first syringe 122 and the second syringe 124 are arranged parallel to one another. The first syringe 122 and the second syringe 124 extend into the coupling mechanism 102. By axially moving the first plunger 126 and the second plunger 128, a sample may be aspirated into the first pipetting tip 108 and/or the second pipetting tip 110 or dispensed therefrom.

Figure 3:
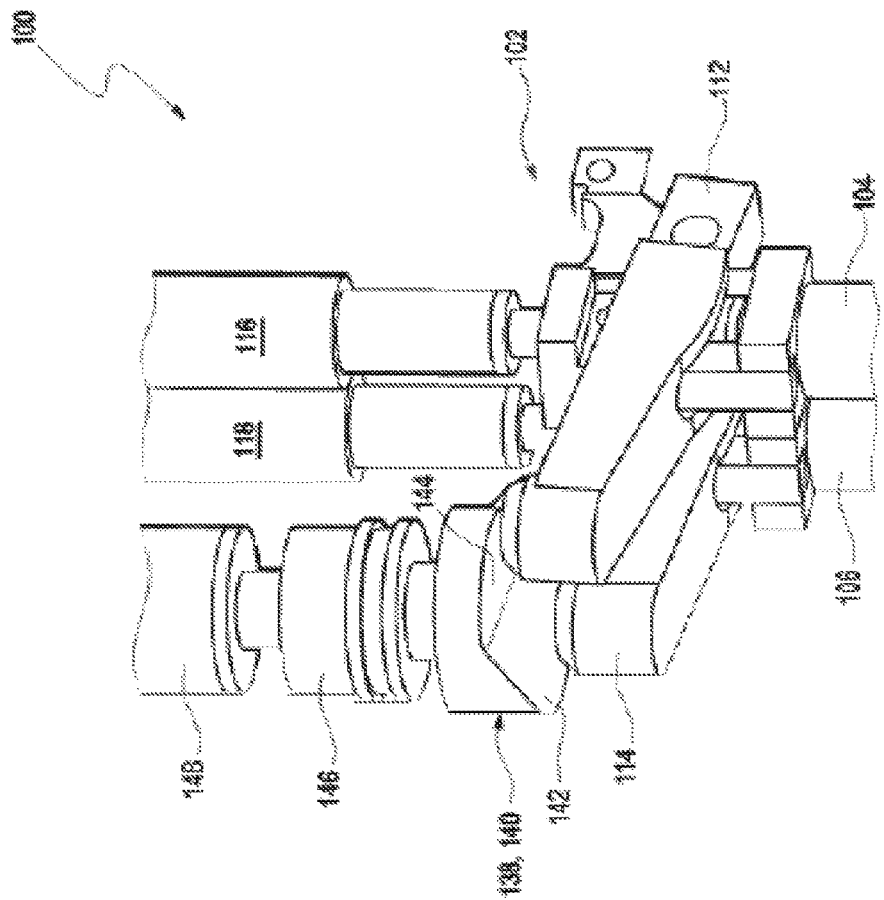
FIG. 3 shows a perspective view of a coupling mechanism and a selection element of the pipetting device.

FIG. 3 shows a perspective view of the coupling mechanism 102 and a selection element 138 of the pipetting device 100. The selection element 138 is adapted to selectively allow coupling of the first coupling unit 104 to release the first coupling unit 104 from the first pipetting tip 108 and to selectively allow a coupling of the second coupling unit 106 to or releasing the second coupling unit 106 from the second pipetting tip 110. As shown in FIG. 3, according to the basic principle of the selection element 138, the selection element 138 is operatively and mechanically coupled to the first coupling unit 104 and the second coupling unit 106. Particularly, the selection element 138 is operatively and mechanically coupled to the first coupling lever 112 and the second coupling lever 114. It is to be noted that for facilitating a better understanding of the basic principle of the present invention, FIG. 3 shows the selection element 138 directly mechanically coupled to the first coupling lever 112 and the second coupling lever 114. As will be described in further detail below, this is not necessarily the case but an indirect coupling of the selection element 138 to the first coupling lever 112 and the second coupling lever 114 by means of a further constructional member is feasible as well. The selection element 138 comprises a rotatory disc 140.

The rotatory disc 140 is formed in a specific shape. Particularly, the rotatory disc 140 is not formed as a pure flat disc but comprises a protrusion 142 and a lowered portion 144. The protrusion 142 and the lowered portion 144 gradually transit into one another so as to prevent any disturbances or obstructions when the rotatory disc 140 and the protrusion moves across the first coupling lever 112 and the second coupling lever 114. The protrusion 142 and the lowered portion 144 are adapted to selectively engage none, one or both of the first coupling lever 112 and the second coupling lever 114. In other words, the first coupling lever 112 may be contacted either by the protrusion 142 or the lowered portion 144 and the second coupling lever 114 may be contacted by the protrusion 142 or lowered portion 144. The respective contacts may be provided in a separate or simultaneous manner. Thus, the first coupling lever 112 is in the engagement position when engaged by the protrusion 142 and is in the release position when engaged by the lowered portion 144. Analogously, the second coupling lever 114 is in the engagement position when engaged by the protrusion 142 and is in the release position when engaged by the lowered portion 144. Particularly, the rotatory disc 140 is rotatable such that the protrusion 142 and the lowered portion 144 are each adapted to selectively engage none, one or both of the first coupling lever 112 and the second coupling lever 114. For this purpose, the rotatory disc 140 is disposed on a rotatable shaft 146 adapted to rotate the rotatory disc 140. The protrusion 142 and the lowered portion 144 gradually transit into one another so as to prevent any disturbances of the operation of the selection element 138 when the rotatory disc 140 is rotated and engages first coupling lever 112 and/or the second coupling lever 114 with the protrusion 142. The pipetting device 100 may further comprise a motor 148 adapted to rotate the shaft 146. The operation of the selection element 138 will be described in further detail below.

FIG. 4 shows the selection element 138 in a first operation state. FIG. 4 shows the rotatory disc 140 in a first rotational position, in which the lowered portion 144 engages the first coupling lever 112 as well as the second coupling lever 114. Thus, the first squeezing device 116 and the second squeezing device 118 are in an unsqueezed position where the first sealing member and the second sealing member are not axially compressed. Particularly, as shown in FIG. 4, the first squeezing device 116 and the second squeezing device 118 are located in an axial upper position. Thus, the first coupling unit 104 is released from or not engaged with the first pipetting tip 108 and the second coupling unit 106 is released from or not engaged with the second pipetting tip 110.

FIG. 5 shows the selection element 138 in a second operation state. FIG. 5 shows the rotatory disc 140 in a second rotational position, in which the protrusion 142 engages the first coupling lever 112 while the lowered portion 144 engages the second coupling lever 114. Thus, the rotatory disc 140 is rotated 90° with respect to the first rotational position. The first squeezing device 116 is located in an axial lower position where the first sealing member is axially compressed so as to be in the prestress force producing engagement with the first inner surface of the first pipetting tip 108 while the second squeezing device 118 is still located in the axial upper position or in the unsqueezed position where the second sealing member is not axially compressed. Thus, the first coupling unit 104 is coupled to or engaged with the first pipetting tip 108 and the second coupling unit 106 is released from or not engaged with the second pipetting tip 110.

Figure 6:
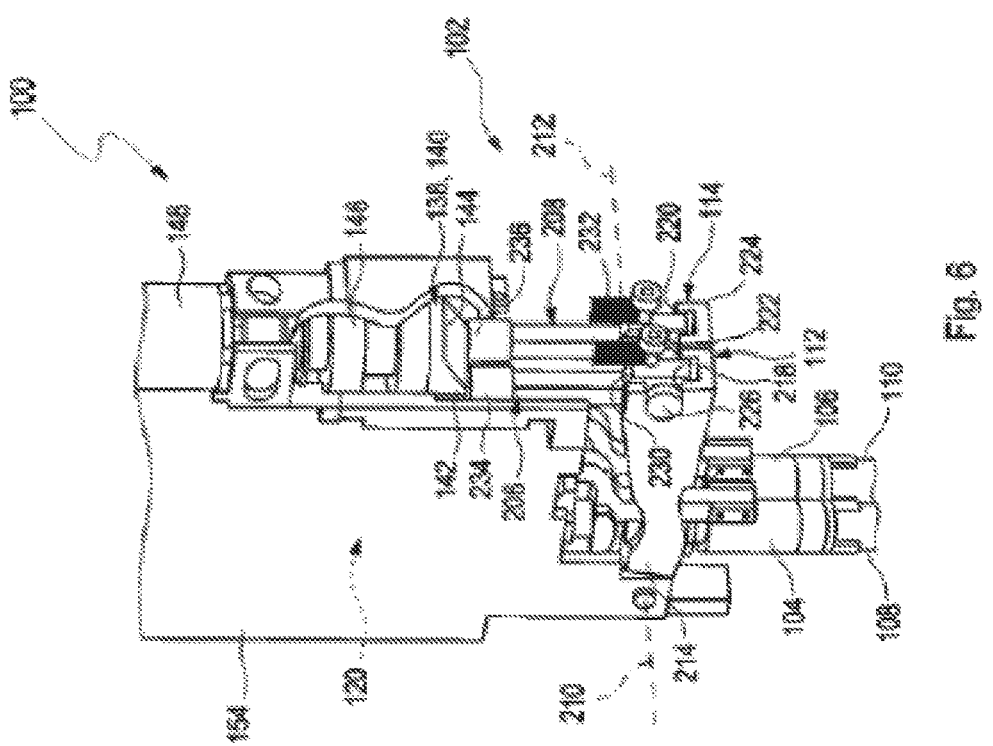
FIG. 6 shows a perspective view of the pipetting device in a third operation state.

FIG. 6 shows the selection element 138 in a third operation state. FIG. 6 shows the rotatory disc 140 in a third rotational position, in which the protrusion 142 engages the first coupling lever 112 as well as the second coupling lever 114. Thus, the rotatory disc 140 is rotated 90° with respect to the second rotational position and 180° with respect to the first rotational position. The first squeezing device 112 are each located in an axial lower position where the first sealing member and the second sealing member are axially compressed so as to be in the prestress force producing engagement with the first inner surface of the first pipetting tip 108 and the second inner surface of the second pipetting tip 110. Thus, the first coupling unit 104 is coupled to or engaged with the first pipetting tip 108 and the second coupling unit 106 is coupled to or engaged with the second pipetting tip 110.

Figure 7:
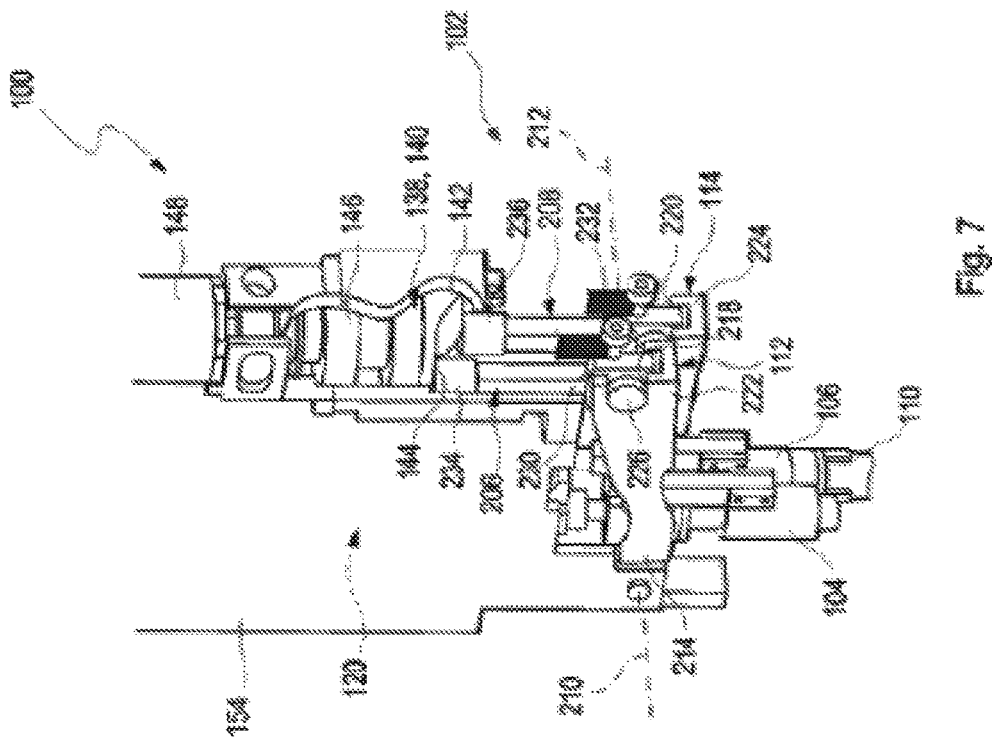
FIG. 7 shows a perspective view of the pipetting device in a fourth operation state.

FIG. 7 shows the selection element 138 in a fourth operation state. FIG. 7 shows the rotatory disc 140 in a fourth rotational position, in which the protrusion 142 engages the second coupling lever 114 while the lowered portion 144 engages the first coupling lever 112. Thus, the rotatory disc 140 is rotated 90° with respect to the first rotational position but is rotated in an opposite direction with respect to a rotational movement direction from the first rotation position into the second rotational position. The second squeezing device 118 is located in an axial lower position where the second sealing member is axially compressed so as to be in the prestress force producing engagement with the second inner surface of the second pipetting tip 110 while the first squeezing device 116 is located in the axial upper position or in the unsqueezed position where the first sealing member is not axially compressed. Thus, the second coupling unit 106 is coupled to or engaged with the second pipetting tip 110 and the first coupling unit 104 is released from or not engaged with the first pipetting tip 108. Summarizing, by rotating the rotatory disc 140, the coupling mechanism 102 is adapted to engage none, one or both of the first pipetting tip 108 and the second pipetting tip 110.

Hereinafter, further aspects of the pipetting device 100 will be described.

FIG. 8 shows a left side perspective view of a pipetting device 100. The pipetting device 100 further comprises a tilt mechanism 150. The tilt mechanism 150 is adapted to move the first coupling unit 104 between an untilted position, in which the first coupling unit 104 and the second coupling unit 106 are arranged parallel to one another, and a tilted position, in which the first coupling unit 104 is tilted relative to the second coupling unit 106.

FIG. 9 shows another left side perspective view of the pipetting device 100. While FIG. 8 shows the first coupling unit 104 in the untilted position, FIG. 2 shows the first coupling unit 104 in the tilted position, in which the first coupling unit 104 is tilted relative to the second coupling unit 106. The pipetting device further comprises a tilt mechanism trigger 152 adapted to trigger the tilt mechanism 150. The pipetting device 100 further comprises a frame 154. The coupling mechanism 102, the tilt mechanism 150 and the tilt mechanism trigger 152 are at least partially arranged within the frame 154 and supported by the frame 154. In one embodiment, the selection element 138 is also at least partially arranged within the frame 154. Particularly, the tilt mechanism 150 is tiltable around a first pivot 156. The first pivot 156 is supported in a correspondingly formed opening 120 located in the frame 154. The opening 158 is located at a side wall of the frame 154. Thus, the tilt mechanism 150 is tiltable together with the first coupling unit 104. In other words, the tilt mechanism 150 is also moveable between an untilted position and a tilted position. In order to prevent collisions of the first pipetting tip 108 or the second pipetting tip 110 with a vessel, it is preferred that the first coupling unit 104 may not only be tilted but may also be locked in each of the untilted and the tilted position. Hereinafter, it will be specified in more detail how the locking of the first coupling unit 104 in each of the untilted position and the tilted position is realized.

Figure 10:
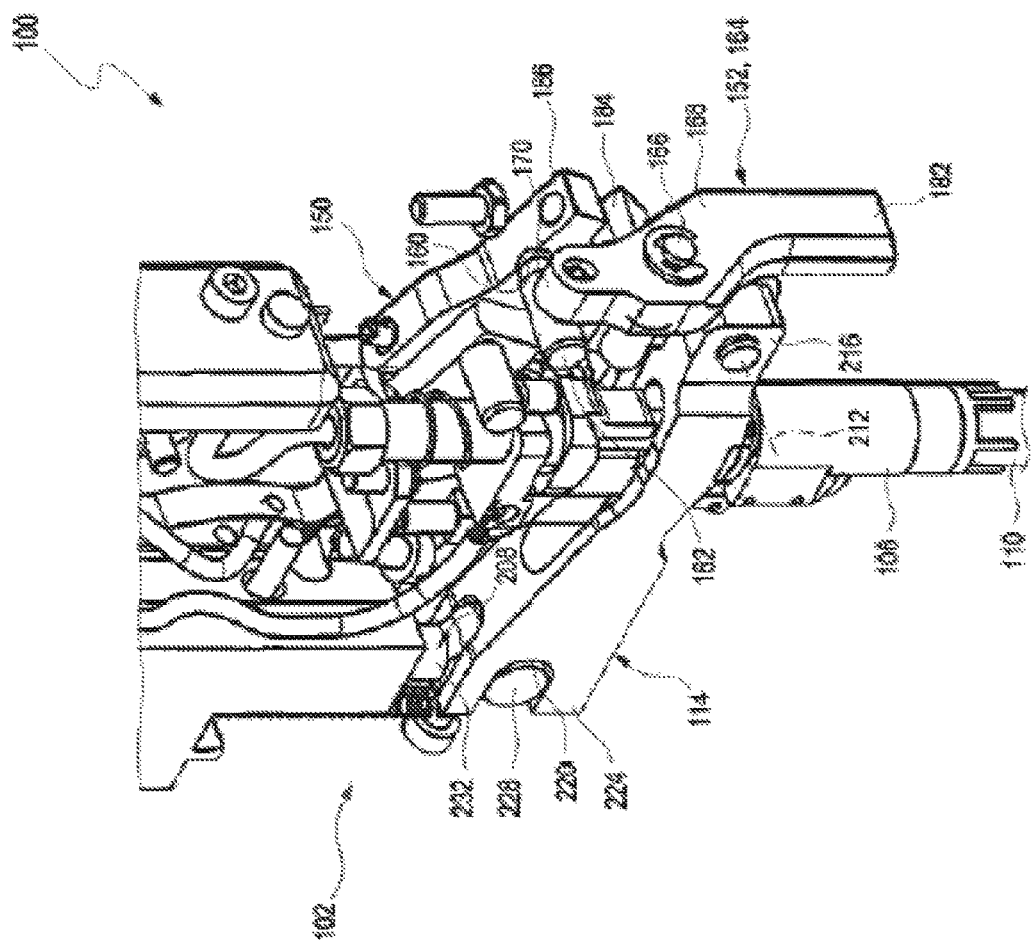
FIG. 10 shows a right side and front perspective view of the pipetting device.

FIG. 10 shows a right side and front perspective view of the pipetting device 100. It is to be noted that the frame 154 is omitted in FIG. 10 in order to facilitate a better understanding of the present invention. The tilt mechanism trigger 152 is adapted to releasably fix the tilt mechanism 150 in the untilted position. Particularly, the tilt mechanism 150 comprises a first recess 160. The tilt mechanism trigger 152 comprises a pin 162. By means of an engagement of the pin 162 with the first recess 160, the tilt mechanism 150 is fixable in the untilted position. Particularly, the tilt mechanism trigger 152 comprises a trigger lever 164 which is adapted to pivot around a second pivot 166. The second pivot 166 may be supported by the frame 154. The second pivot 166 is arranged perpendicular with respect to the first pivot 156. For example, the second pivot 166 is located at a front wall of the frame 154. Particularly, the pin 162 is connected to the trigger lever 164. By means of disengagement of the pin 162 from the first recess 160, the tilt mechanism 150 is releasable from the untilted position. The pin 162 is selectively engageable with and disengageable from the first recess 160 by means of pivoting the trigger lever 164 around the second pivot 166.

As can be taken from FIG. 10, the second pivot 166 is disposed in a middle portion 168 of the trigger lever 164. The pin 162 is disposed at an upper end 170 of the trigger lever 164. FIG. 10 shows the pin 162 engaged with the first recess 160. If the trigger lever 164 is pivoted around the second pivot 166 in a counterclockwise direction with respect to the illustration of FIG. 10, the upper end 170 moves to the left with respect to the illustration of FIG. 10. Thus, the pin 162 also moves to the left and is released from the first recess 160. Analogously, if the trigger lever 164 is pivoted in a clockwise direction around the second pivot 166, the upper end 170 moves to the right such that the pin 162 also moves to the right. Then the pin 162 engages with the first recess 160 such that the tilt mechanism 150 is blocked from tilting.

Further, the tilt mechanism 150 is releasably fixable in the tilted position. As shown in FIGS. 8 and 9, the coupling mechanism 102 further comprises a first coupling unit protrusion 172 disposed on the first coupling unit 104. The first coupling unit protrusion 172 may be formed as a collar. The first coupling lever 112 comprises a first coupling lever recess 174. By means of engagement of the first coupling unit protrusion 172 with the first coupling lever recess 174, the tilt mechanism 150 is releasably fixable in the tilted position. Analogously, by means of disengagement of the first coupling unit protrusion 172 from the first coupling lever recess 174, the tilt mechanism 150 is releasable from the tilted position.

By means of pivoting the tilt mechanism 150 around the first pivot 156, the first coupling unit protrusion 172 is selectively engageable with and disengageable from the first coupling lever recess 174. For example, with respect to the illustration of FIGS. 8 and 9, if the tilt mechanism 150 is pivoted in a counterclockwise direction around the first pivot 156, the first coupling unit 104 is moved from the untilted position to the tilted position. Further, the first coupling unit protrusion 172 is moved into an engagement with the first coupling lever recess as shown in FIG. 9. Analogously, starting from FIG. 9, if the tilt mechanism 150 is pivoted in a clockwise direction around the first pivot 156, the first coupling unit 104 is moved from the tilted position into the untilted position and the first coupling unit protrusion 172 is disengaged from the first coupling lever recess 174.

Figure 11:
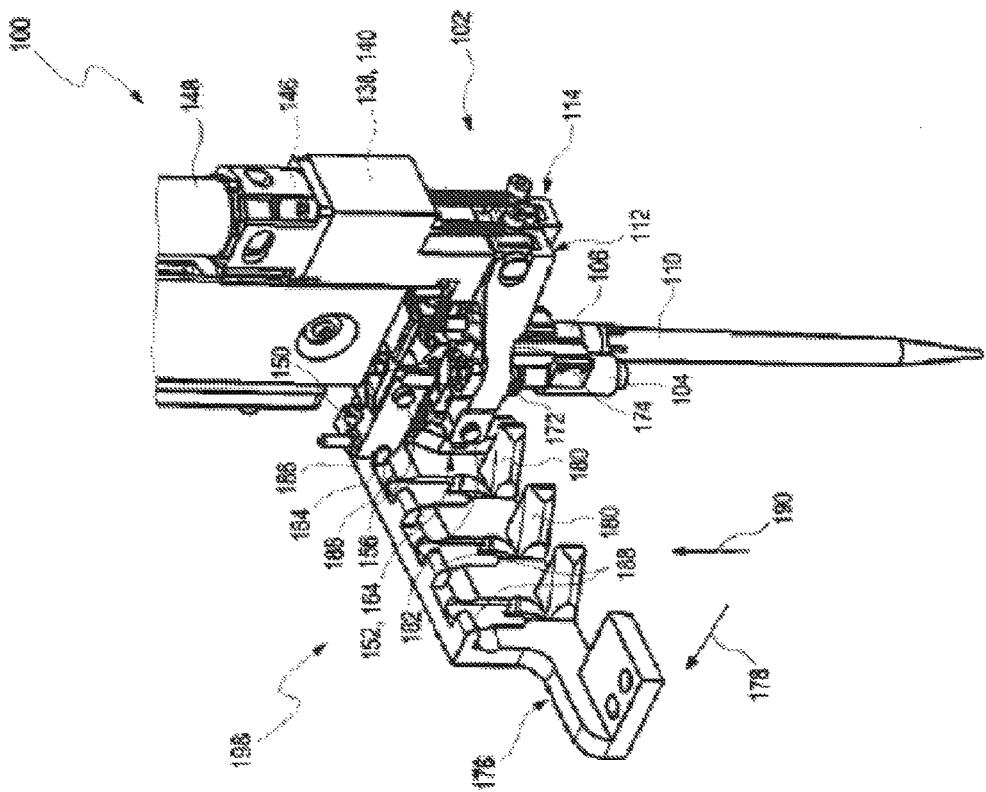
FIG. 11 shows a left side and rear perspective view of the pipetting device.

FIG. 11 shows a left side and rear perspective view of the pipetting device 100. It is to be noted that the frame 154 is omitted in FIG. 11 in order to facilitate a better understanding of the present invention. In order to realize the tilting movement of the tilt mechanism 150, the present invention provides an activation device 176. More particularly, the tilt mechanism trigger 152 is adapted to be activated by means of a movement of the pipetting device 100 relative to the activation device 176 in a first direction 178. It is to be noted that the activation device 176 is stationary with respect to the pipetting device 100. As can be taken from FIG. 11, the activation device 176 comprises at least one inclined surface 180. When the pipetting device 100 is moved in the first direction 178 towards the activation device 176, the inclined surface 180 engages a lower end 182 of the trigger lever 164. It is to be noted that the inclined surface 180 which engages the lower end 182 is hidden by the lower end in the illustration of FIG. 11. The inclined surface 180 causes the trigger lever 164 to pivot around the second pivot 166 in a clockwise direction with respect to the illustration of FIG. 11, which corresponds to a counterclockwise direction with respect to the illustration of FIG. 10.

Figure 12:
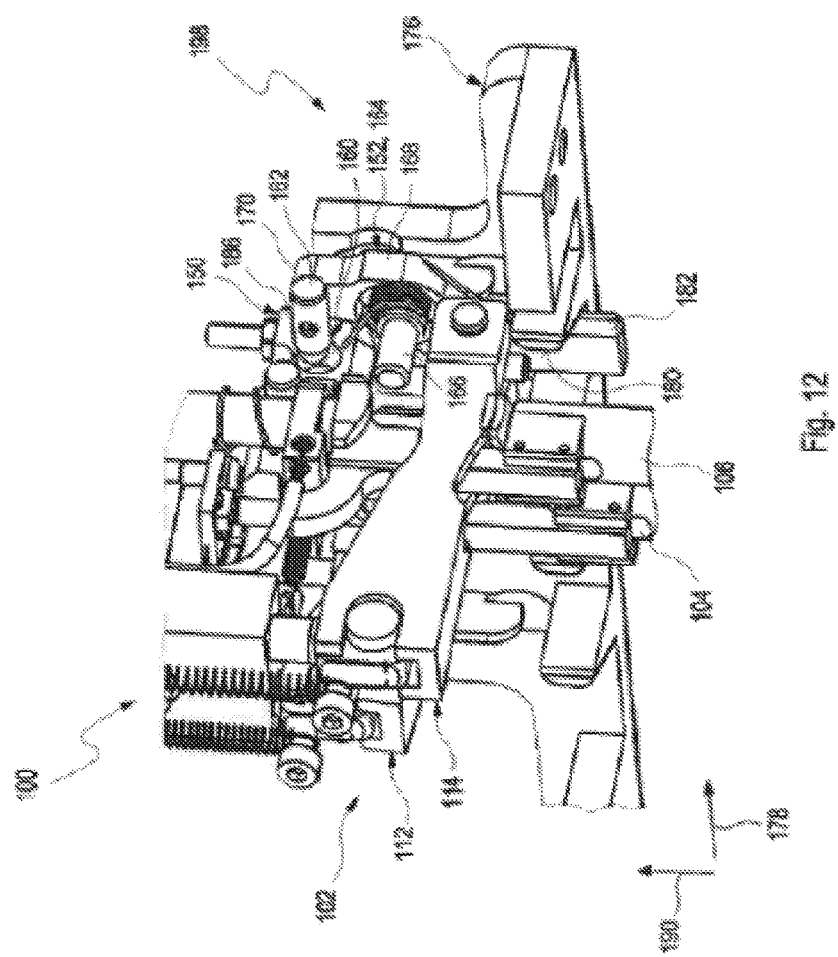
FIG. 12 shows a right side and rear perspective view of the pipetting device.

FIG. 12 shows a right side and rear perspective view of the pipetting device 100. It is to be noted that the frame 154 is omitted in FIG. 12 in order to facilitate a better understanding of the present invention. By the engagement of the inclined surface 180 with the lower end 182 of the trigger lever 164, the pin 162 is released from the first recess 160 in the manner as described above. FIG. 12 shows the pin 162 moved out of the first recess 160. Thus, the movement of the pipetting device 100 in the first direction 178 towards the activation device 176 serves to release the fixation of the tilt mechanism 150. In order to tilt the tilt mechanism 150, another process in connection with the activation device 176 is realized.

Figure 13:
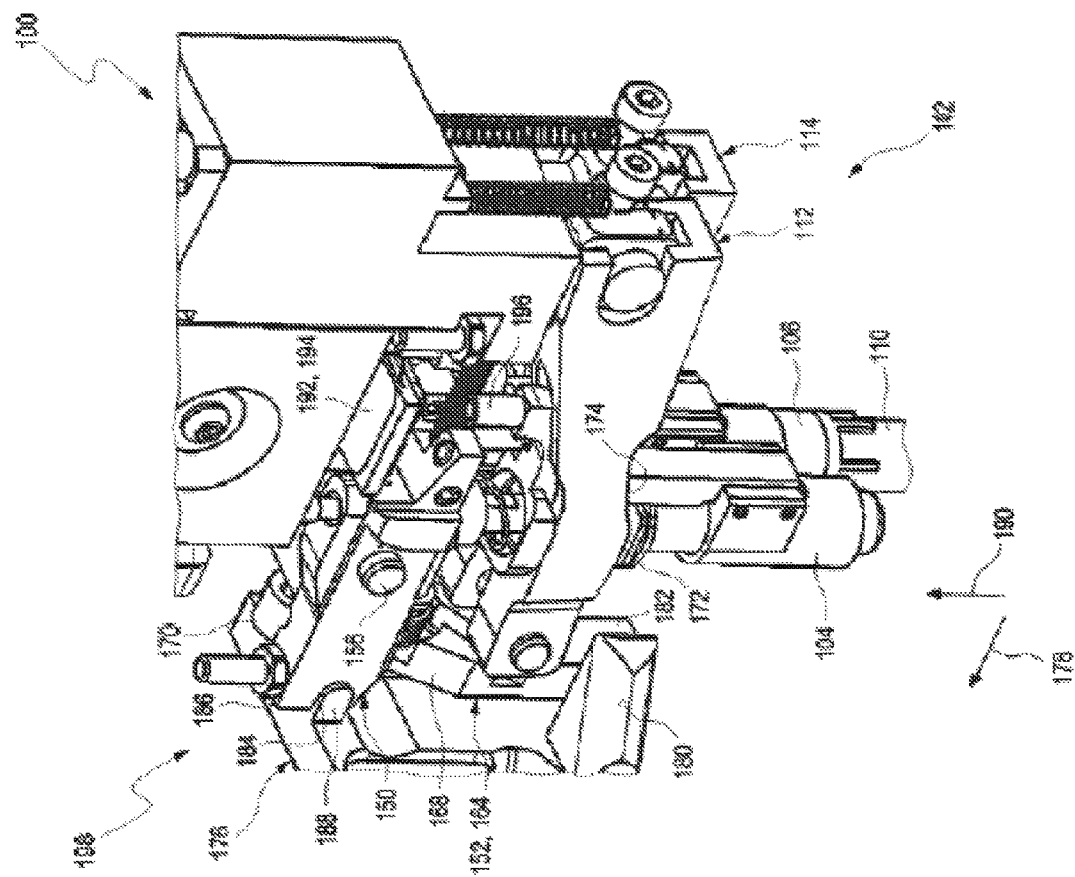
FIG. 13 shows a left side and rear perspective view of the pipetting device.

FIG. 13 shows a left side rear perspective view of the pipetting device 100. It is to be noted that the frame 154 is omitted in FIG. 13 in order to facilitate a better understanding of the present invention. Particularly, the tilt mechanism 150 comprises a second recess 184 arranged at a front end 186 of the tilt mechanism 150. The front end 186 faces the activation device 176. The activation device 176 comprises a protrusion 188. The protrusion 188 is arranged above the inclined surface 180. The second recess 184 is engageable with the protrusion 188. By means of a movement of the pipetting device 100 relative to the activation device 176 in a second direction 190 with the second recess 184 engaged with the protrusion 188, the tilt mechanism 150 is tiltable around the first pivot 156 in the manner described above. The second direction 190 is different from the first direction 178. More particularly, the second direction 190 is perpendicular to the first direction 178.

If the pipetting device 100 is moved in the second direction 190 corresponding to an upward movement with respect to the illustration of FIG. 13, the front end 186 is moved downwards with the second recess 184 engaged with the protrusion 188 such that the tilt mechanism 150 pivots in counterclockwise direction around the first pivot 156. This construction allows for omitting an additional actuator for realizing the tilt movement of the tilt mechanism 150. Needless to say, according to an alternative embodiment of the present invention (not shown in detail), the tilt mechanism 150 may be tiltable around the first pivot 156 by means of an actuator. Further, as shown in FIG. 13, the pipetting device 100 may comprise a sensor 192 for detection whether the first coupling unit 104 is in the untilted position or the tilted position. The sensor 192 may be a Hall sensor 194. For this purpose, a magnet 196 may be arranged at the tilt mechanism 150. If the magnet 196 faces the Hall sensor 194, the Hall sensor 194 will output a signal indicating that the first coupling unit 104 is in the untilted position. If the magnet 196 does not face the Hall sensor 194 because the magnet 196 has been moved away from the Hall sensor 194, the Hall sensor 194 will not output a signal indicating that the first coupling unit 104 is in the tilted position.

FIG. 14 shows a schematic illustration of an apparatus 198 for processing a sample or reagent. The pipetting device 100 may be part of the apparatus 198. The apparatus 198 further comprises an input 205 for a first vessel 200, which comprises a sample or reagent, and a holder 202 for holding a second vessel 204 to which the sample or reagent is transferrable by means of the pipetting device 100. The first vessel 200 and/or the second vessel 204 may be formed as a tube. The apparatus 198 for processing a sample further comprises the activation device 176. The activation device 176 may be arranged at the first vessel 200. Alternatively, the activation device 176 may be arranged spaced apart from the first vessel 200.

With the pipetting device according to the present invention, the sample or reagent may be pipetted. Particularly, the first pipetting tip 108 may optionally be coupled to the first coupling unit 104 or not whereas the second pipetting tip 110 is coupled to the second coupling unit 106. Such a coupling process is well known to the skilled person such that a description of the coupling process is omitted. Then, the first coupling unit 104 is moved from the untilted position into the tilted position such that the first coupling unit 104 is tilted relative to the second coupling unit 106. Then, a sample or reagent from the first vessel 200 is aspirated by means of the second pipetting tip 110. Particularly, the first coupling unit 104 is moved into the tilted position if a ratio of a length of the second pipetting tip 110 and a target immersion depth of the second pipetting tip 110 into the first vessel 200 is below a predetermined threshold. In other words, if the second pipetting tip 110 is not long enough in order to comply with a target immersion depth, then the first coupling unit 104 is moved into the tilted position in order to avoid a collision of the first coupling 104 unit with the first vessel 200 into which the second pipetting tip 110 is immersed. In case the first coupling unit 104 has to be moved into the tilted position, the first pipetting tip 108 is not coupled to the first coupling unit 104. Finally, the pipetting device 100 is moved to the second vessel 204 and the sample or reagent is dispensed from the second pipetting tip 110 into the second vessel 204. Thus, the sample or reagent is transferred from the first vessel 200 to the second vessel 204 by means of the pipetting device 100.

As mentioned above, FIG. 3 shows the selection element 138 directly mechanically coupled to the first coupling lever 112 and the second coupling lever 114. FIG. 3 is intended to explain the cooperation of the selection element 138 with the first coupling lever 112 and the second coupling lever 114. FIGS. 4 to 13 show a constructional alternative, wherein the selection element 138 is indirectly mechanically coupled to the first coupling lever 112 and the second coupling lever 114. More particularly, the selection element 138 is mechanically coupled to the first coupling lever 112 and the second coupling lever 114 by means of a first connection member 206 and a second connection member 208. The first connection member 206 and the second connection member 208 may optionally be provided for reasons explained in further detail hereinafter. As mentioned above, the first coupling lever 112 and the second coupling lever 114 are each movable between an engagement position and a release position. This kind of movement is not a linear movement but a pivotal movement. More particularly, the first coupling lever 112 is pivotally moveable around a first pivotal axis 210 and the second coupling lever 114 is pivotally moveable around a second pivotal axis 212. The first pivotal axis 210 extends at a front end 214 of the first coupling lever 112 and the second pivotal axis 212 extends at a front end 216 of the second coupling lever 114. The first pivotal axis 210 and the second pivotal axis 212 may overlap one another. Thus, the first coupling lever 112 and the second coupling lever 114 are moveable on a circular path around the first pivotal axis 210 and the second pivotal axis 212, respectively. The first coupling lever 112 further comprises a first insertion hole 218 and the second coupling lever 114 comprises a second insertion hole 220. The first insertion hole 218 is located at a rear end 222 of the first coupling lever 112. The second insertion hole 220 is located at a rear end 224 of the second coupling lever 114 (FIG. 10). The first connection member 206 comprises a first connection member protrusion 226. The second connection member 208 comprises a second connection member protrusion 228 (FIG. 10). The first connection member protrusion 226 is located at a lower end 230 of the first connection member 206 and adapted to be inserted into the first insertion hole 218. Thus, the first connection member 206 is connected to the first coupling lever 112. The second connection member protrusion 228 is located at a lower end 232 of the second connection member 208 and adapted to be inserted into the second insertion hole 220. An upper end 234 of the first connection member 206, which is opposite to the lower end 230, is connected to the rotatory disc 140. Similarly, an upper end 236 of the second connection member 208, which is opposite to the lower end 232, is connected to the rotatory disc 140. Thus, the first connection member 206 and the second connection member 208 are each connected to the selection element 138 and the rotatory disc 140, respectively.

The first coupling lever 112 is also pivotally moveable around the first connection member protrusion 226 and the second coupling lever 114 is also pivotally moveable around the second connection member protrusion 228. Further, the first connection member protrusion 226 is slightly moveable within the first insertion hole 218 and the second connection member protrusion 228 is slightly moveable within the second insertion hole 220. Thus, a movement of the first coupling lever 112 and the second coupling 114 along a surface of the rotatory disc 140, which might cause deviations from an exact engagement of the protrusion 142 and the lowered portion 114 with the first coupling lever 112 and the second coupling 114, is prevented by means of the first connection member 206 and the second connection member 208. More particularly, the first connection member 206 and the second connection member 208 are linearly moveable in upwards and downwards directions by means of rotating the rotatory disc 140 while the movement on the circular path of the first coupling lever 112 and the second coupling lever 114 is compensated. Thus, the upper ends 234, 236 of the first connection member 206 and the second connection member 208 remain at the same position within a plane perpendicular to the shaft 146 but these do not move laterally with respect to the rotatory disc 140. It is to be noted that the upper ends 234, 236 of the first connection member 206 and the second connection member 208 may be rounded such that the contacting surface with the rotatory disc 140 is always the same independent from the rotational position of the rotatory disc 140 relative to the first connection member 206 and the second connection member 208.

It is explicitly stated that the coupling mechanism 102 may comprise more than the first coupling unit 104 and the second coupling unit 106. In other words, the coupling mechanism 102 may comprise more than two coupling units in order to allow to couple more than two pipetting tips to the coupling units. For example, the coupling mechanism 102 may comprise 4, 6, 8, 10 or even more coupling units in order to allow for coupling of 4, 6, 8, 10 or even more pipetting tips. In this case, the pipetting device 100 comprises a plurality of selection elements 138 which may be designed in the above manner so as to allow to operate several pairs of two coupling units.

FIG. 15 a) to i) shows another embodiment of the selection element. The selection element comprises a linear shifting block (300) which comprises protrustions (301, 302) in the bottom surface (303) adapted to selectively engage none, one or both of the first coupling lever (112) and the second coupling lever (114). In one embodiment, a central recess (304) is located between two protrusions (301, 302) on the bottom surface (303) of the shifting block (300). This permits the rapid selection of either the right (112) or the left (114) coupling lever to move into the lowered position. In FIG. 15 a), the first connection member (206) and the second connection member (208) are both located in the central recess (304). From this position, the linear shifting block (300) can move either to the right, such that coupling lever (112) is moved to the lowered position (FIG. 15 b) and further moved to the right such that both coupling levers (112, 114) are moved to the lowered position (FIG. 15 c), and further movement to the right allows to select coupling lever (114) to be in the lowered position, while coupling lever (112) is not (FIG. 15 d). With a further movement of the linear shifting block (300), none of the coupling levers (112, 114) is selected to be in the lowered position (FIG. 15 e). FIG. 15 f) to i) show the movement of the linear shifting block (300) in the opposite direction, allowing to selectively move either coupling lever (114) (FIG. 15 f), both coupling levers (114, 112) (FIG. 15 g), coupling lever (112) (FIG. 15 h), or none of the coupling levers (112, 114) (FIG. 15 i), into the lowered position. The linear shifting block (300), thus, permits selection of the coupling lever (112 or 114) to be moved to the lowered position by contacting the corresponding connection member (206, 208) with one of the protrusions (301, 302), and/or selection of the coupling lever (112, 114) that should not be moved into the lowered position by contacting the corresponding connection member (206, 208) with the bottom surface (303) that does not correspond to a protrusion (301, 302).

FIG. 16 (a) to 16(l) show the movement of tilt mechanism 150, trigger lever 164 and first coupling unit 104 upon activation with the activation device 176.

FIG. 16(a) shows the trigger lever 164 position when the coupling unit 104 is in the untilted position and pin 162 is in the locked position. When the pin 162 is in the locked position, the tilt mechanism 150 cannot be moved. FIG. 16(b) corresponds to FIG. 16 (a), except that the activation device was removed from the drawing to better show the mechanism. FIG. 16 (c) shows a close-up from the left side of the pipetting device shown in FIGS. 16(a) and 16(b) with the trigger lever 164, first coupling unit 104 and tilt mechanism 150 in the unactivated position and pin 162 in the locked position.

FIG. 16(d) shows the activation of the trigger lever 164 by the activation device 176. The lower part of the activation device 176 moves the lower part of the trigger lever 164, thereby moving the trigger 152 lever counter-clockwise, and thus, moving pin 162 into the unlocked position. FIG. 16(e) corresponds to FIG. 16(d), except that the activation device was removed from the drawing to better show the mechanism. FIG. 16(f) shows a close-up from the left side of the pipetting device shown in FIGS. 16(d) and 16(e) with the trigger lever 164 moved counter-clockwise, first coupling unit 104 still in the untilted position, pin 162 in the unlocked position and tilt mechanism 150 in the unactivated position.

FIG. 16(g) shows the device after movement of the tilt mechanism 150 and first coupling unit 104 when the activation device 176 is moved downwards relative to the trigger lever 164. The tilt mechanism 150 is moved downwards, thereby tilting the first coupling unit 104. The trigger lever 164 remains stationary in this step. FIG. 16(h) corresponds to FIG. 16(g), except that the activation device was removed from the drawing to better show the mechanism. FIG. 16(i) shows a close-up from the left side of the pipetting device shown in FIGS. 16(g) and 16(h), where the tilt mechanism 150 is in a lower position compared to the previous states, and first coupling unit 104 is partly tilted.

FIG. 16(j) shows the device after movement of the first coupling unit 104 into the final tilt position. Activation device 176 is moved even further downwards compared to FIG. 16(g). By this, the tilt mechanism 150 is also moved further downwards compared to FIG. 16(g), and the first coupling unit 104 is tilted more than in FIG. 16(g). The trigger lever 164 remains stationary in this step, so does pin 162, which remains in the unlocked position. FIG. 16(k) corresponds to FIG. 16(j), except that the activation device was removed from the drawing to better show the mechanism. FIG. 16(l) shows a close-up from the left side of the pipetting device shown in FIGS. 16(k) and 16(j), where the tilt mechanism 150 is in a lower position compared to FIG. 16(i), and first coupling unit 104 is fully tilted.

FIG. 16(m) shows the tilted pipetting device after removal of the activation de-vice 176. The trigger lever 164 moves slightly clockwise, and, thereby, pin 162 is moved into the locked position. This leads to a locking of the tilt mechanism 150 in the lowest position and a locking of the first coupling unit 104 in the tilted position. FIG. 16(n) corresponds to FIG. 16(m), except that the activation device was removed from the drawing to better show the mechanism. FIG. 16(o) shows a close-up from the left side of the pipetting de-vice shown in FIGS. 16(m) and 16(n), where the trigger lever 164 is slightly moved clockwise, compared to FIG. 16(i), the tilt mechanism 150 is in its lowest position and first coupling unit 104 is fully tilted and pin 162 is seen, which is now in the locked position, thereby locking the fully tilted first coupling unit 104 in its tilted position.

The present application is not to be limited in scope by the specific embodiments described herein. Indeed, various modifications in addition to those described herein will become apparent to those skilled in the art from the foregoing description and accompanying figures. Such modifications are intended to fall within the scope of the claims. Various publications are cited herein, the disclosures of which are incorporated by reference in their entireties.

The invention claimed is:

1. A pipetting device for an apparatus for processing a sample or reagent comprising:
    a coupling mechanism comprising a first coupling lever connected to a first coupling unit adapted to be coupled to a first pipetting tip, and a second coupling lever connected to a second coupling unit adapted to be coupled to a second pipetting tip, and a selection element to selectively couple or release the first and second pipetting tips, respectively, to or from the first and second coupling units, respectively,
wherein the selection element is a single constructional member that does not comprise other parts or components,
wherein the selection element is indirectly mechanically coupled to the first coupling unit and the second coupling unit, and
wherein the selection element is adapted to control attachment or release of either one or the other pipetting tip or both of the pipetting tips or none of the pipetting tips, because the first coupling lever is moveable between an engagement position, in which the first coupling unit is adapted to be coupled to the first pipetting tip, and a release position, in which the first coupling unit is adapted to be released from the first pipetting tip, wherein the second coupling lever is moveable between an engagement position, in which the second coupling unit is adapted to be coupled to the second pipetting tip, and a release position, in which the second coupling unit is adapted to be released from the second pipetting tip.

2. The pipetting device of claim 1, wherein the selection element comprises a rotatory disc (140), wherein the rotatory disc (140) moves across the first coupling lever and the second coupling lever, wherein the rotatory disc (140) is not formed as a pure flat disc of uniform thickness, but instead, wherein the rotatory disc (140) comprises a protrusion (142) and a lowered portion (144), wherein the protrusion (142) and lowered portion (144) are both located on a bottom surface of the rotatory disc, wherein the protrusion (142) and the lowered portion (144) on the bottom surface are of different thicknesses, wherein the protrusion (142) is thicker than the lowered portion (144), wherein the rotatory disc (140) is adapted to selectively engage none, one, or both of the first coupling lever and the second coupling lever, and wherein the protrusion (142) and the lowered portion (144) are continuous with respect to each other and gradually transition into one another, such that the lowered portion (144) gradually increases in thickness as the lowered portion (144) gradually transitions into the protrusion (142), around the rotatory disc (140), and such that the protrusion (142) gradually decreases in thickness as the protrusion (142) gradually transitions into the lowered portion (144), around the rotatory disc (140), so as to prevent any disturbances or obstructions when the rotatory disc (140) selectively engages none, one, or both of the first coupling lever and the second coupling lever.

3. The pipetting device of claim 2, wherein the first coupling lever is in the engagement position when engaged by the protrusion and is in the release position when engaged by the lowered portion, wherein the second coupling lever is in the engagement position when engaged by the protrusion and is in the release position when engaged by the lowered portion.

4. The pipetting device of claim 2, wherein the rotatory disc is rotatable such that the protrusion and the lowered portion are each adapted to selectively engage none, one or both of the first coupling lever and the second coupling lever.

5. The pipetting device of claim 3, wherein the rotatory disc is disposed on a rotatable shaft adapted to rotate the rotatory disc.

6. The pipetting device of claim 5, further comprising a motor adapted to rotate the rotatable shaft.

7. The pipetting device of claim 1, further comprising a first syringe and a second syringe, wherein the first syringe comprises a first plunger and the second syringe comprises a second plunger, and an actuator adapted to operate the first plunger and the second plunger.

8. The pipetting device of claim 7, wherein the first syringe and the second syringe extend into the coupling mechanism.

9. The pipetting device of claim 1, further comprising a frame including the following elements arranged within and supported by the frame:
a coupling mechanism including at least a first coupling unit adapted to be coupled to a first pipetting tip and a second coupling unit adapted to be coupled to a second pipetting tip,
a tilt mechanism configured to move the first coupling unit between an untilted position, in which the first coupling unit and the second coupling unit are arranged parallel to one another, and a tilted position, in which the first coupling unit is tilted relative to the second coupling unit, and
a tilt mechanism trigger adapted to trigger the tilt mechanism by engagement with an activation device,
wherein movement of the pipetting device relative to the activation device engages with and activates the tilt mechanism, fixing the tilt mechanism in the untilted position, and thereby fixing the first coupling unit in the untilted position.

10. The pipetting device of claim 9, wherein the tile mechanism is tiltable around a first pivot.

11. The pipetting device of claim 9, wherein the tilt mechanism is releasably fixable in the tilted position.

12. The pipetting device of claim 10, wherein the coupling mechanism further comprises a first coupling unit protrusion disposed on the first coupling unit, wherein the first coupling lever comprises a first coupling lever recess, wherein the tilt mechanism is releasably fixable in the tilted position by means of engagement of the first coupling unit protrusion with the first coupling lever recess.

13. An apparatus for processing a sample or reagent, comprising a pipetting device of claim 1, an input for a first vessel, said first vessel comprising a sample or reagent, and a holder for holding a second vessel to which the sample or reagent is transferrable by the pipetting device.

14. A method for pipetting a sample or reagent using a pipetting device of claim 1, comprising
selectively operating the selection element so as to allow the first coupling unit to be coupled to a first pipetting tip,
selectively operating the selection element so as to allow the second coupling unit to be coupled to a second pipetting tip,
aspirating a first sample or reagent from a first vessel by means of the first pipetting tip, and/or
aspirating a second sample or reagent from a second vessel by means of the second pipetting tip.

* * * * *